United States Patent
Michaels et al.

(10) Patent No.: US 8,460,256 B2
(45) Date of Patent: Jun. 11, 2013

(54) COLLAPSIBLE FLUID COLLECTION AND DISPOSAL SYSTEM AND RELATED METHODS

(75) Inventors: Thomas L. Michaels, McCullom Lake, IL (US); Russ A. Johnson, Spring Grove, IL (US); Eric D. Hill, Gurnee, IL (US)

(73) Assignee: Allegiance Corporation, McGaw Park, IL (US)

( * ) Notice: Subject to any disclaimer, the term of this patent is extended or adjusted under 35 U.S.C. 154(b) by 115 days.

(21) Appl. No.: 12/837,297

(22) Filed: Jul. 15, 2010

(65) Prior Publication Data

US 2011/0118680 A1 May 19, 2011

Related U.S. Application Data

(60) Provisional application No. 61/225,812, filed on Jul. 15, 2009.

(51) Int. Cl.
*A61M 1/00* (2006.01)
*A47L 5/00* (2006.01)
*F16J 15/16* (2006.01)

(52) U.S. Cl.
USPC ............ 604/317; 604/38; 604/121; 604/141; 604/143; 15/300.1; 137/565.23; 210/416.1; 277/311

(58) Field of Classification Search
None
See application file for complete search history.

(56) References Cited

U.S. PATENT DOCUMENTS

| | | | |
|---|---|---|---|
| 687,790 A | 12/1901 | Scales | |
| 1,703,834 A | 2/1929 | Thompson | |
| 2,057,238 A | 10/1936 | Krug | |
| 2,452,503 A * | 10/1948 | Teetor | ........................... 277/463 |
| 2,686,625 A | 8/1954 | Sundholm | |
| 3,035,623 A | 5/1962 | Goetz | |
| 3,164,186 A | 1/1965 | Weber et al. | |
| 3,307,746 A | 3/1967 | Edwards | |
| 3,397,648 A | 8/1968 | Henderson | |
| 3,515,127 A | 6/1970 | Raymond | |

(Continued)

FOREIGN PATENT DOCUMENTS

| | | |
|---|---|---|
| CN | 1199192 | 11/1988 |
| CN | 1398469 | 2/2003 |

(Continued)

OTHER PUBLICATIONS

Baatz, S. et al., Hand off Support for mobility with IP over Bluetooth, Univ of Bonn, Inst. of Computer Sci IV (2000 IEEE), pp. 143-154.

(Continued)

*Primary Examiner* — Melanie Hand
*Assistant Examiner* — Joshua Lee
(74) *Attorney, Agent, or Firm* — Arent Fox LLP

(57) ABSTRACT

A fluid collection system includes a disposable collection container and a disposable collection container receiving housing, the housing having a cavity and a suction source. The fluid collection container may include a flexible liner and a shelf for diverting fluid from the suction and to assist with a collapse of the liner during evacuation of the fluid from the liner. The collection container receiving housing may include a piston assembly having a main piston body and a scraper ring. The collection container receiving housing may include a piston stop feature. The system may include a partially hydrophobic filter and a flat surface suction tool.

17 Claims, 23 Drawing Sheets

U.S. PATENT DOCUMENTS

| | | | |
|---|---|---|---|
| 3,537,455 A | 11/1970 | Skyles et al. | |
| 3,773,211 A | 11/1973 | Bridgman | |
| 3,780,738 A | 12/1973 | Deaton | |
| 3,804,090 A * | 4/1974 | Holbrook | 604/86 |
| 3,814,098 A | 6/1974 | Deaton | |
| 3,830,238 A | 8/1974 | Kurtz et al. | |
| 3,915,189 A | 10/1975 | Holbrook et al. | |
| 3,924,772 A | 12/1975 | Magnani | |
| 4,015,603 A * | 4/1977 | Kurtz et al. | 604/318 |
| 4,022,258 A | 5/1977 | Steidley | |
| 4,173,295 A | 11/1979 | Steinmann | |
| 4,181,140 A * | 1/1980 | Bayham et al. | 137/68.28 |
| 4,321,922 A * | 3/1982 | Deaton | 604/319 |
| 4,340,049 A * | 7/1982 | Munsch | 604/29 |
| 4,346,711 A | 8/1982 | Agdanowski et al. | |
| 4,379,455 A | 4/1983 | Deaton | |
| 4,392,860 A | 7/1983 | Huck et al. | |
| 4,397,643 A | 8/1983 | Rygiel | |
| 4,419,093 A | 12/1983 | Deaton | |
| 4,455,140 A | 6/1984 | Joslin | |
| 4,460,361 A | 7/1984 | Nichols | |
| 4,492,313 A | 1/1985 | Touzani | |
| 4,515,283 A | 5/1985 | Suzuki | |
| 4,541,457 A | 9/1985 | Blenkush | |
| 4,568,006 A | 2/1986 | Mueller et al. | |
| 4,569,674 A | 2/1986 | Phillips et al. | |
| 4,578,060 A | 3/1986 | Huck et al. | |
| 4,642,128 A | 2/1987 | Solorzano | |
| 4,650,477 A | 3/1987 | Johnson | |
| 4,769,019 A | 9/1988 | Rosenblatt | |
| 4,775,366 A | 10/1988 | Rosenblatt | |
| 4,790,453 A | 12/1988 | Fontana et al. | |
| 4,799,924 A | 1/1989 | Rosenblatt | |
| 4,799,925 A | 1/1989 | Rosenblatt | |
| 4,863,446 A | 9/1989 | Parker | |
| 4,874,023 A | 10/1989 | Ulm | |
| 4,888,728 A | 12/1989 | Shirakawa et al. | |
| 4,906,261 A | 3/1990 | Mohajer | |
| 4,921,679 A | 5/1990 | Martin et al. | |
| 4,925,447 A | 5/1990 | Rosenblatt | |
| 4,928,245 A | 5/1990 | Moy et al. | |
| 4,930,997 A | 6/1990 | Bennett | |
| 4,948,010 A | 8/1990 | Wiggins | |
| 4,950,247 A | 8/1990 | Rosenblatt | |
| 4,957,491 A | 9/1990 | Parker | |
| 4,957,492 A | 9/1990 | McVay | |
| 4,963,134 A | 10/1990 | Bachscheider et al. | |
| 4,976,694 A | 12/1990 | Schreibman | |
| 4,979,628 A | 12/1990 | Robbins, III | |
| 4,980,913 A | 12/1990 | Skret | |
| 4,981,473 A | 1/1991 | Rosenblatt | |
| 4,986,839 A | 1/1991 | Wertz et al. | |
| 5,002,534 A | 3/1991 | Rosenblatt | |
| 5,010,179 A | 4/1991 | Lai | |
| 5,014,389 A * | 5/1991 | Ogilvie et al. | 15/353 |
| 5,027,963 A | 7/1991 | Robbins, III | |
| 5,039,494 A | 8/1991 | Martin et al. | |
| 5,071,409 A * | 12/1991 | Rosenberg | 604/119 |
| 5,072,762 A | 12/1991 | Jimenz | |
| 5,084,250 A | 1/1992 | Hall | |
| 5,124,126 A | 6/1992 | Ripp | |
| 5,156,602 A | 10/1992 | Steffler | |
| 5,173,442 A | 12/1992 | Carey | |
| 5,178,828 A | 1/1993 | Uesugi | |
| 5,185,007 A | 2/1993 | Middaugh et al. | |
| 5,192,272 A * | 3/1993 | Faure | 604/141 |
| 5,209,565 A | 5/1993 | Goncalves | |
| 5,217,038 A | 6/1993 | Pinder | |
| 5,217,688 A | 6/1993 | Von Lersner | |
| 5,234,419 A | 8/1993 | Bryant et al. | |
| 5,242,434 A | 9/1993 | Terry | |
| 5,242,474 A | 9/1993 | Herbst et al. | |
| 5,252,290 A | 10/1993 | Uesugi | |
| 5,268,666 A | 12/1993 | Michel et al. | |
| 5,269,030 A | 12/1993 | Pahno et al. | |
| 5,279,602 A | 1/1994 | Middaugh et al. | |
| 5,295,518 A | 3/1994 | Baker et al. | |
| 5,309,924 A | 5/1994 | Peabody | |
| 5,318,516 A | 6/1994 | Cosmescu | |
| 5,330,464 A * | 7/1994 | Mathias et al. | 604/415 |
| 5,333,761 A | 8/1994 | Davis et al. | |
| 5,370,270 A | 12/1994 | Adams et al. | |
| 5,380,289 A | 1/1995 | Hemstreet et al. | |
| 5,417,655 A | 5/1995 | Divilio et al. | |
| 5,423,779 A | 6/1995 | Yeh | |
| 5,438,721 A | 8/1995 | Pahno et al. | |
| 5,470,324 A | 11/1995 | Cook et al. | |
| 5,494,074 A | 2/1996 | Ramacier, Jr. et al. | |
| 5,514,119 A | 5/1996 | Curtis | |
| 5,519,858 A | 5/1996 | Walton et al. | |
| 5,520,668 A | 5/1996 | Greff et al. | |
| 5,522,808 A | 6/1996 | Skalla | |
| 5,549,585 A | 8/1996 | Maher et al. | |
| 5,551,001 A | 8/1996 | Cohen et al. | |
| 5,588,167 A | 12/1996 | Pahno et al. | |
| 5,607,411 A | 3/1997 | Heironimus et al. | |
| 5,620,428 A * | 4/1997 | Hand | 604/317 |
| 5,637,103 A | 6/1997 | Kerwin et al. | |
| 5,645,540 A | 7/1997 | Henniges et al. | |
| 5,653,270 A | 8/1997 | Burrows | |
| 5,669,892 A | 9/1997 | Keogh et al. | |
| 5,683,371 A | 11/1997 | Hand | |
| 5,685,835 A | 11/1997 | Brugger | |
| 5,688,255 A | 11/1997 | Hand | |
| 5,720,078 A * | 2/1998 | Heintz | 15/415.1 |
| 5,741,237 A | 4/1998 | Walker | |
| 5,741,238 A | 4/1998 | Bradbury et al. | |
| 5,776,118 A | 7/1998 | Seifert et al. | |
| 5,776,260 A | 7/1998 | Dunn et al. | |
| 5,785,044 A | 7/1998 | Meador et al. | |
| 5,792,126 A | 8/1998 | Tribastone et al. | |
| 5,797,506 A | 8/1998 | Lehmkuhl et al. | |
| 5,807,230 A | 9/1998 | Argenta et al. | |
| 5,807,359 A | 9/1998 | Bemis et al. | |
| 5,808,885 A | 9/1998 | Dew et al. | |
| 5,830,198 A | 11/1998 | Henniges et al. | |
| 5,835,723 A | 11/1998 | Andrews et al. | |
| 5,836,909 A | 11/1998 | Cosmescu | |
| 5,855,289 A | 1/1999 | Moore | |
| 5,859,847 A | 1/1999 | Dew et al. | |
| 5,867,555 A | 2/1999 | Popescu et al. | |
| 5,871,476 A | 2/1999 | Hand | |
| 5,885,240 A | 3/1999 | Bradbury et al. | |
| 5,901,717 A | 5/1999 | Dunn et al. | |
| 5,906,025 A * | 5/1999 | Johnson | 15/415.1 |
| 5,910,291 A | 6/1999 | Skalla et al. | |
| 5,914,047 A | 6/1999 | Griffiths | |
| 5,931,822 A | 8/1999 | Bemis et al. | |
| 5,944,703 A | 8/1999 | Dixon et al. | |
| 5,945,004 A | 8/1999 | Ohira et al. | |
| 5,947,171 A | 9/1999 | Woodruff | |
| 5,968,032 A | 10/1999 | Sleister | |
| 5,975,096 A | 11/1999 | Dunn et al. | |
| 5,985,009 A | 11/1999 | Marsala | |
| 5,997,733 A | 12/1999 | Wilbur et al. | |
| 6,006,272 A | 12/1999 | Aravamudan et al. | |
| 6,017,493 A | 1/2000 | Cambron et al. | |
| 6,024,124 A | 2/2000 | Braun et al. | |
| 6,027,490 A | 2/2000 | Radford et al. | |
| 6,039,724 A | 3/2000 | Seifert et al. | |
| 6,045,596 A | 4/2000 | Holland, Jr. et al. | |
| 6,056,731 A | 5/2000 | Koetke et al. | |
| 6,058,106 A | 5/2000 | Cudak et al. | |
| 6,078,952 A | 6/2000 | Fielding et al. | |
| 6,082,401 A | 7/2000 | Braun et al. | |
| 6,105,093 A | 8/2000 | Rosner et al. | |
| 6,105,638 A | 8/2000 | Edwards et al. | |
| 6,136,098 A * | 10/2000 | Tribastone | 134/21 |
| 6,152,902 A * | 11/2000 | Christian et al. | 604/320 |
| 6,160,808 A | 12/2000 | Maurya | |
| 6,161,578 A | 12/2000 | Braun et al. | |
| 6,180,000 B1 | 1/2001 | Wilbur et al. | |
| 6,203,590 B1 | 3/2001 | Byrd et al. | |
| 6,231,089 B1 | 5/2001 | DeCler et al. | |
| 6,233,248 B1 | 5/2001 | Sautter et al. | |
| 6,244,311 B1 | 6/2001 | Hand et al. | |
| 6,258,232 B1 | 7/2001 | Hasegawa et al. | |

| Patent/Pub No. | Date | Name |
|---|---|---|
| 6,261,276 B1 | 7/2001 | Reitsma |
| 6,263,887 B1 | 7/2001 | Dunn |
| 6,280,867 B1 | 8/2001 | Elias |
| 6,331,246 B1 | 12/2001 | Beckham et al. |
| 6,358,232 B1 | 3/2002 | Hand et al. |
| 6,366,583 B2 | 4/2002 | Rowett et al. |
| 6,368,310 B1 | 4/2002 | Bemis et al. |
| 6,415,313 B1 | 7/2002 | Yamada et al. |
| 6,453,687 B2 | 9/2002 | Sharood et al. |
| 6,488,675 B1 | 12/2002 | Radford et al. |
| 6,494,391 B2 | 12/2002 | Mosenson et al. |
| 6,494,869 B1 | 12/2002 | Hand et al. |
| 6,499,495 B2 | 12/2002 | Jeng |
| 6,501,180 B1 | 12/2002 | Kitch |
| 6,507,953 B1 | 1/2003 | Horlander et al. |
| 6,522,654 B2 | 2/2003 | Small |
| 6,524,307 B1 | 2/2003 | Palmerton et al. |
| 6,588,436 B2 | 7/2003 | Dunn et al. |
| 6,615,243 B1 | 9/2003 | Megeid et al. |
| 6,618,764 B1 | 9/2003 | Shteyn |
| 6,626,877 B2 | 9/2003 | Anderson et al. |
| 6,631,476 B1 | 10/2003 | Vandesteeg et al. |
| 6,652,495 B1 | 11/2003 | Walker |
| 6,672,477 B2 | 1/2004 | Miller et al. |
| 6,673,055 B2 | 1/2004 | Bemis et al. |
| 6,676,644 B2 | 1/2004 | Ikeda |
| 6,705,591 B2 | 3/2004 | DeCler |
| 6,706,198 B2 | 3/2004 | Gershenson |
| 6,721,900 B1 | 4/2004 | Lenner et al. |
| 6,731,201 B1 | 5/2004 | Bailey et al. |
| 6,735,619 B1 | 5/2004 | Sawada |
| 6,755,807 B2 | 6/2004 | Risk, Jr. et al. |
| 6,759,946 B2 | 7/2004 | Sahinoglu et al. |
| 6,770,061 B2 | 8/2004 | Wildman |
| 6,776,175 B2 | 8/2004 | Dunn et al. |
| 6,793,222 B2 * | 9/2004 | Katsaounis et al. .......... 277/459 |
| 6,800,074 B2 | 10/2004 | Henley et al. |
| 6,824,533 B2 | 11/2004 | Risk, Jr. et al. |
| 6,842,430 B1 | 1/2005 | Melnik |
| 6,854,053 B2 | 2/2005 | Burkhardt et al. |
| 6,856,999 B2 | 2/2005 | Flanagin et al. |
| 6,891,850 B1 | 5/2005 | Vandesteeg et al. |
| 6,893,425 B2 | 5/2005 | Dunn et al. |
| 6,902,673 B2 | 6/2005 | Smit et al. |
| 6,909,891 B2 | 6/2005 | Yamashita et al. |
| 6,915,444 B2 | 7/2005 | Vasko et al. |
| 6,934,740 B1 | 8/2005 | Lawande et al. |
| 6,976,977 B2 | 12/2005 | Yam |
| 6,982,960 B2 | 1/2006 | Lee et al. |
| 6,987,462 B2 | 1/2006 | Bae et al. |
| 7,035,270 B2 | 4/2006 | Moore, Jr. et al. |
| 7,058,722 B2 | 6/2006 | Ikami et al. |
| 7,062,531 B2 | 6/2006 | Kim |
| 7,069,091 B2 | 6/2006 | Williamson |
| 7,090,663 B2 | 8/2006 | Dunn et al. |
| 7,107,358 B2 | 9/2006 | Vasko et al. |
| 7,111,100 B2 | 9/2006 | Ellerbrock |
| 7,114,518 B2 * | 10/2006 | Kirby .......... 137/504 |
| 7,115,115 B2 | 10/2006 | Bemis et al. |
| 7,148,142 B1 | 12/2006 | Dakshina-Murthy et al. |
| 7,149,792 B1 | 12/2006 | Hansen et al. |
| 7,163,618 B2 | 1/2007 | Beckham et al. |
| 7,200,683 B1 | 4/2007 | Wang et al. |
| 7,257,104 B2 | 8/2007 | Shitama |
| 7,258,711 B2 | 8/2007 | Dunn et al. |
| 7,287,062 B2 | 10/2007 | Im et al. |
| 7,294,839 B2 * | 11/2007 | Rich et al. .......... 250/343 |
| 7,308,644 B2 | 12/2007 | Humpleman et al. |
| 7,328,816 B2 | 2/2008 | Shannon et al. |
| 7,353,259 B1 | 4/2008 | Bakke et al. |
| 7,389,332 B1 | 6/2008 | Muchow et al. |
| 7,389,358 B1 | 6/2008 | Matthews et al. |
| 7,403,994 B1 | 7/2008 | Vogl et al. |
| 7,412,538 B1 | 8/2008 | Eytchison et al. |
| 7,421,478 B1 | 9/2008 | Muchow |
| 7,430,591 B2 | 9/2008 | Chamberlain |
| 7,437,494 B2 | 10/2008 | Ellerbrock |
| 7,454,517 B2 | 11/2008 | Ha et al. |
| 7,461,164 B2 | 12/2008 | Edwards et al. |
| 7,468,330 B2 | 12/2008 | Allen et al. |
| 7,469,727 B2 | 12/2008 | Marshall |
| 7,497,340 B2 | 3/2009 | Hershberger et al. |
| 7,673,030 B2 | 3/2010 | Hite et al. |
| 7,673,153 B1 | 3/2010 | Oishi et al. |
| 2001/0025322 A1 | 9/2001 | Song et al. |
| 2002/0011923 A1 | 1/2002 | Cunningham et al. |
| 2002/0021465 A1 | 2/2002 | Moore, Jr. et al. |
| 2002/0026528 A1 | 2/2002 | Lo |
| 2002/0035624 A1 | 3/2002 | Kim |
| 2002/0038358 A1 | 3/2002 | Sweatt, III et al. |
| 2002/0059617 A1 | 5/2002 | Terakado et al. |
| 2002/0082569 A1 | 6/2002 | Wildman |
| 2002/0103898 A1 | 8/2002 | Moyer et al. |
| 2002/0118696 A1 | 8/2002 | Suda |
| 2002/0120763 A1 | 8/2002 | Miloushev et al. |
| 2002/0127780 A1 | 9/2002 | Ma et al. |
| 2002/0165989 A1 | 11/2002 | Etoh |
| 2002/0193144 A1 | 12/2002 | Belski et al. |
| 2003/0009537 A1 | 1/2003 | Wang |
| 2003/0014630 A1 | 1/2003 | Spencer et al. |
| 2003/0037166 A1 | 2/2003 | Ueno et al. |
| 2003/0038730 A1 | 2/2003 | Imafuku et al. |
| 2003/0051053 A1 | 3/2003 | Vasko et al. |
| 2003/0051203 A1 | 3/2003 | Vasko et al. |
| 2003/0053477 A1 | 3/2003 | Kim et al. |
| 2003/0054809 A1 | 3/2003 | Bridges et al. |
| 2003/0065824 A1 | 4/2003 | Kudo |
| 2003/0067910 A1 | 4/2003 | Razazian et al. |
| 2003/0079000 A1 | 4/2003 | Chamberlain |
| 2003/0079001 A1 | 4/2003 | Chamberlain |
| 2003/0083758 A1 | 5/2003 | Williamson |
| 2003/0085795 A1 | 5/2003 | An |
| 2003/0088703 A1 | 5/2003 | Kim |
| 2003/0158956 A1 | 8/2003 | Tanaka et al. |
| 2003/0165142 A1 | 9/2003 | Mills et al. |
| 2004/0023162 A1 | 2/2004 | Hasegawa et al. |
| 2004/0042487 A1 | 3/2004 | Ossman |
| 2004/0047298 A1 | 3/2004 | Yook et al. |
| 2004/0055105 A1 * | 3/2004 | Park et al. .......... 15/353 |
| 2004/0064578 A1 | 4/2004 | Boucher et al. |
| 2004/0088731 A1 | 5/2004 | Putterman et al. |
| 2004/0102743 A1 | 5/2004 | Walker |
| 2004/0111490 A1 | 6/2004 | Im et al. |
| 2004/0116902 A1 | 6/2004 | Grossman et al. |
| 2004/0129338 A1 * | 7/2004 | Rohret et al. .......... 141/89 |
| 2004/0158333 A1 | 8/2004 | Ha et al. |
| 2004/0164076 A1 | 8/2004 | Baker et al. |
| 2004/0184456 A1 | 9/2004 | Binding et al. |
| 2004/0204693 A1 | 10/2004 | Anderson et al. |
| 2004/0205309 A1 | 10/2004 | Watanabe |
| 2004/0224261 A1 | 11/2004 | Resnick et al. |
| 2005/0069696 A1 | 3/2005 | King et al. |
| 2005/0108568 A1 | 5/2005 | Bussiere et al. |
| 2005/0139532 A1 | 6/2005 | Hershberger et al. |
| 2005/0170269 A1 | 8/2005 | Nakagawa et al. |
| 2005/0171495 A1 | 8/2005 | Austin et al. |
| 2005/0183780 A1 * | 8/2005 | Michaels et al. .......... 137/565.22 |
| 2005/0187528 A1 | 8/2005 | Berg |
| 2005/0187529 A1 | 8/2005 | Reasoner et al. |
| 2005/0189283 A1 | 9/2005 | Smit et al. |
| 2005/0189288 A1 | 9/2005 | Hershberger et al. |
| 2005/0190727 A1 | 9/2005 | Vanlieshout et al. |
| 2005/0202350 A1 | 9/2005 | Colburn et al. |
| 2005/0215961 A1 | 9/2005 | Romano et al. |
| 2005/0250052 A1 | 11/2005 | Nguyen |
| 2006/0030681 A1 * | 2/2006 | Sawyer et al. .......... 525/471 |
| 2006/0036219 A1 | 2/2006 | Alvin |
| 2006/0047677 A1 | 3/2006 | Lin et al. |
| 2006/0156836 A1 * | 7/2006 | Ny et al. .......... 73/866.5 |
| 2006/0156918 A1 * | 7/2006 | Dahl .......... 92/240 |
| 2006/0248106 A1 | 11/2006 | Kundert |
| 2006/0271709 A1 | 11/2006 | Vasko et al. |
| 2007/0019615 A1 | 1/2007 | Baek et al. |
| 2007/0025368 A1 | 2/2007 | Ha et al. |
| 2007/0032058 A1 | 2/2007 | Sung |
| 2007/0038191 A1 | 2/2007 | Burbank et al. |
| 2007/0135778 A1 | 6/2007 | Murray et al. |
| 2007/0135779 A1 | 6/2007 | Lalomia et al. |

| | | | |
|---|---|---|---|
| 2008/0053539 | A1 | 3/2008 | Hershberger et al. |
| 2008/0097631 | A1 | 4/2008 | Baek et al. |
| 2008/0222325 | A1 | 9/2008 | Ishino et al. |
| 2008/0255692 | A1 | 10/2008 | Hofrichter et al. |
| 2008/0259786 | A1 | 10/2008 | Gonda |
| 2009/0005747 | A1 | 1/2009 | Michaels et al. |
| 2009/0012485 | A1 | 1/2009 | Michaels et al. |
| 2009/0159535 | A1 | 6/2009 | Hershberger et al. |

FOREIGN PATENT DOCUMENTS

| | | | |
|---|---|---|---|
| EP | 1 115 263 | A1 | 7/2001 |
| EP | 1 202 493 | A2 | 5/2002 |
| EP | 1 387 215 | A2 | 2/2004 |
| GB | 2 233 494 | A | 1/1991 |
| JP | 60-112336 | | 6/1985 |
| JP | 61-216543 | | 9/1986 |
| JP | 9295651 | A | 11/1997 |
| JP | 2002-325079 | | 11/2002 |
| KR | 10-2001-0093265 | | 10/2001 |
| KR | 10-2002-0064847 | | 8/2002 |
| KR | 10-2003-0040766 | | 5/2003 |
| WO | 80/01558 | A1 | 8/1980 |
| WO | 98/55164 | A1 | 12/1998 |
| WO | 01/03178 | A1 | 1/2001 |
| WO | 01/50825 | A1 | 7/2001 |
| WO | 01/80030 | A1 | 10/2001 |
| WO | 02/09350 | A3 | 3/2002 |
| WO | 02/09755 | A2 | 12/2002 |
| WO | 02/097555 | A3 | 12/2002 |
| WO | 03/030252 | A2 | 4/2003 |
| WO | 2005/031855 | A1 | 4/2005 |
| WO | 2008/094703 | A2 | 8/2008 |

OTHER PUBLICATIONS

Ganz et al., "Q-Soft: software framework for QoS support in home networks," Computer Nov. 1998, pp. 1-66.

Hwang et al., "ATM-based plug-and-play technique for in-home networking," Electronics Letters, vol. 34, No. 22, pp. 2088-2090, 1998.

International Search Report & Written Opinion issued in PCT/US2008/03817, dated Jun. 20, 2008 11 pages.

International Search Report issued in PCT/US2008/03818, dated Jul. 30, 2008, 13 pages.

Invitation to Pay Additional Fees & Partial Search Report issued in PCT/US2007/008371, mailed Oct. 29, 2007, 4 pages.

Kent et al., "Security Architecture for the Internet Protocol," Network Working Group, Nov. 1998, pp. 1-66.

Kim et al., "Home Networking Digital TV Based on LnCP," IEEE Transaction on Consumer Electronics, vol. 48, No. 4, Nov. 2002, pp. 990-996.

Lee et al., "A New Control Protocol for Home Appliance LnCP" International Symposium on Industrial Electronics, 2001, Proceedings, ISIE 2001, Jun. 12-16, 2001 pp. 286-291.

Lee et al., "A New Home Network Protocol Controlling and Monitoring Home Appliance—HNCP," IEEE, 2002, pp. 312-313.

Lee et al., "Home Network Control Protocol for Networked Home Appliance and Its Application," IEEE, pp. 1-7, 2002.

Letter from Foreign Associate dated Jun. 26, 2008, with Official Translation of Communication issued in DE 10 2006 030 267.2, dated May 26, 2008, 3 pages.

Letter from Foreign Associate dated Oct. 19, 2007, with Official Translation of Communication issued in DE 10 2006 030 267.2, dated Sep. 13, 2007, 4 pages.

Manner et al., "Evaluation of Mobility and quality of service interaction," The International Journal of Computer and Telecommunications Networking, vol. 38, No. 2, pp. 137-163, 2002.

Neptune 2 Ultra, Waste Management System, 2 pages; as viewed at http://www.stryker.com/stellent/groups/instruments/documents/web_prod/059445.pdf, Feb. 21, 2008, pp. 1-2.

Wang et al., "Towards Dependable Home Networking: An Experience Report," IEEE, 2000, pp. 43-48.

Written Opinion of the ISA issued in PCT/US2007/008371, 4 pages.

\* cited by examiner

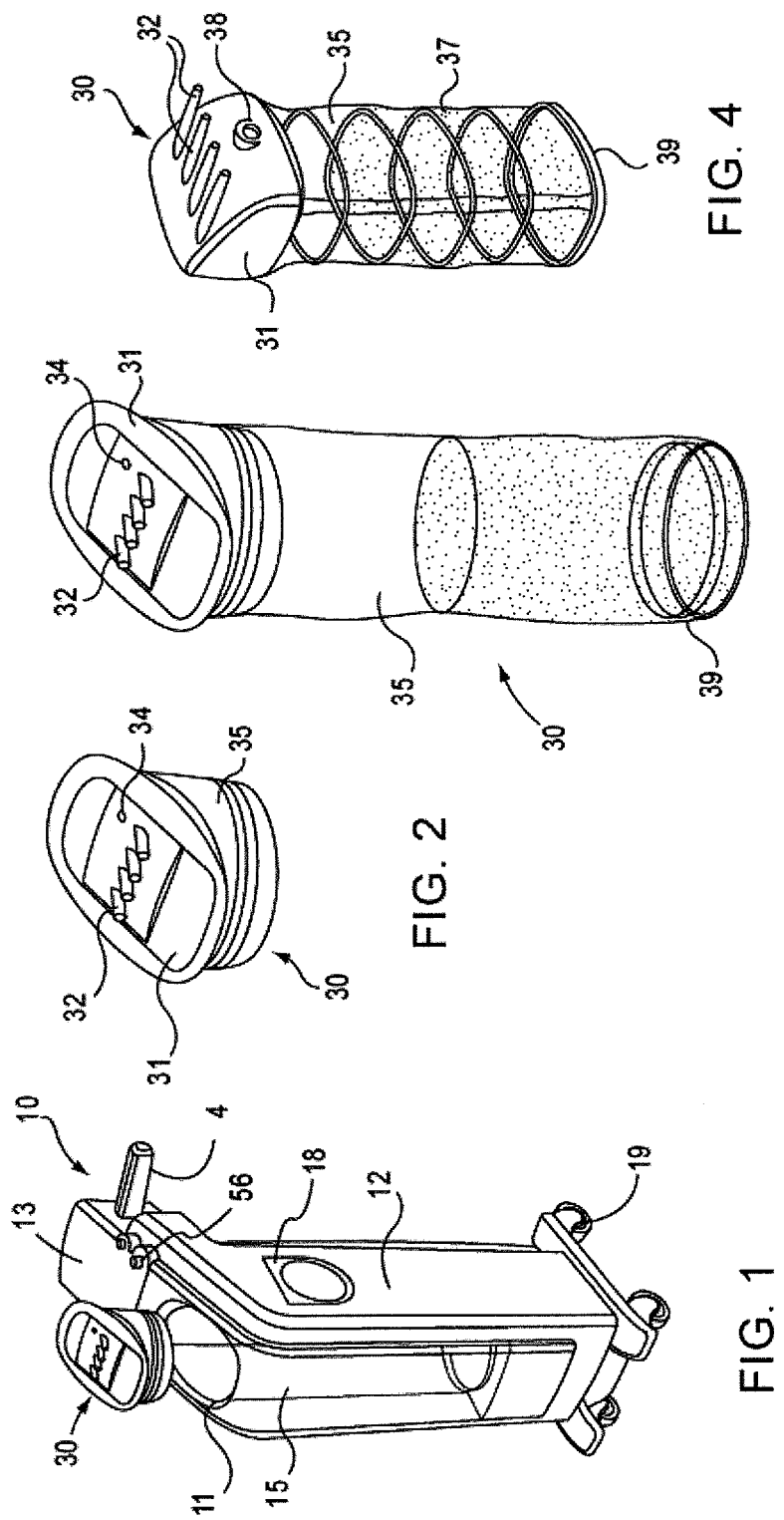

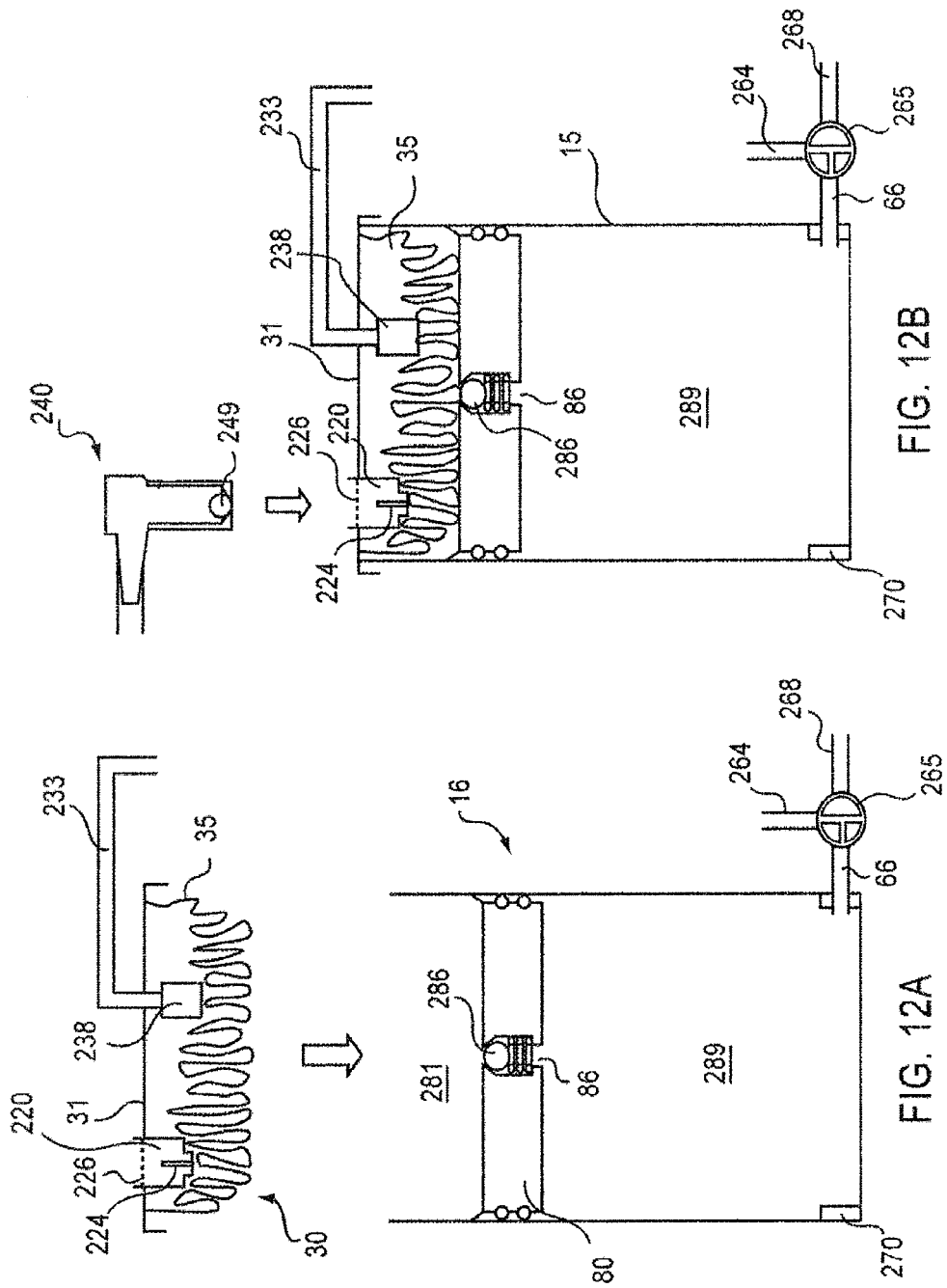

COLLAPSIBLE FLUID COLLECTION AND DISPOSAL SYSTEM AND RELATED METHODS

CLAIM OF PRIORITY UNDER 35 U.S.C. §119

This application claims the benefit of U.S. Provisional Application Ser. No. 61/225,812, entitled "FLUID COLLECTION AND DISPOSAL SYSTEM AND RELATED METHODS" and filed on Jul. 15, 2009, which is expressly incorporated by reference herein in its entirety.

BACKGROUND OF THE INVENTION

1. Technical Field of the Invention

Aspects of the present invention relate generally to fluid collection and disposal systems and related methods. More specifically, particular aspects relate to liquid collection and disposal systems that utilize flexible liners and related methods of use thereof.

2. Brief Description of Related Art

Hospital operating rooms, emergency rooms, and other healthcare facilities generate a large volume of liquid waste, which may include irrigation liquids and secretions removed from a patient's body (e.g., blood and other bodily liquids). To collect and dispose of such liquid waste, suction canisters are typically used. A typical suction canister is a temporary storage container that uses suction to create a negative pressure inside the canister to drain liquids or secretions from the patients' body. After each medical procedure (e.g., surgery), the canister containing the liquid waste is transported to a utility area to be disposed of as red-bag waste or to be emptied, cleaned, and disinfected for reuse. A new or cleaned canister is then brought into the operating room for a next medical procedure. This process can be labor intensive and time consuming. Furthermore, since this process is performed following every medical procedure, the frequency of the process may increase the clinicians' risk of exposure to potentially hazardous waste.

Accordingly, there is a need for an improved waste collection and disposal system that may overcome one or more of the problems discussed above.

SUMMARY OF THE INVENTION

Among others, various aspects of the invention may include providing a fluid collection system that utilizes disposable flexible liners to reduce the volume of medical wastes. Another aspect may include providing a lid for a fluid collection system that automatically connects to a suction source. Also, certain aspects of the invention may provide a waste disposal system, for use with the fluid collection system that may improve labor efficiency, safety, and convenience of the medical personnel participating in a medical procedure. In particular, the fluid collection systems and waste disposal systems in accordance with aspects of the present invention may provide a clean and convenient interface between the source of waste and the waste disposal station, thereby reducing the risk of exposure to potentially hazardous waste.

While aspects and exemplary aspects of the present invention will be described in connection with a particular medical waste collection and disposal process, various aspects of the invention may be used in other suitable medical and non-medical applications, such as medical or non-medical cleaning devices and processes.

Aspects may include a fluid collection container, including a flexible liner; a lid attached to the flexible liner such that the lid and flexible liner define a substantially sealed interior space therebetween, the lid having: a first opening configured for communication with a first access port of a suction instrument through which the collection container receives fluid; a second opening configured for communication with a second access port of a suction source; a rupturable evacuation port for communication with a disposal station through which collected fluid is removed from the collection container; and a shelf formed on the surface of the lid facing the liner.

The shelf may be located between the first opening and the second opening, wherein the shelf extends from a surface of the lid a sufficient distance to divert collected fluids away from the access port of the suction source. The shelf may be shaped to direct fluid entering the first opening toward the liner. The fluid collection container may further include a screen formed on the surface of the lid facing the liner surrounding the evacuation port, and the shelf may be further shaped to prevent the liner from collapsing against at least a portion of the screen during removal of the collected fluid.

Aspects further include a mobile waste disposal system, including a mobile frame; a suction source; a first connector attached to the mobile frame configured to receive a water line; a second connector attached to the mobile frame configured to receive a waste depository line; and a third connector, attached to the mobile frame, configured to communicate the suction source with an opening in a lid of a collapsible fluid collection container, wherein the suction source is configured to evacuate contents of the collapsible fluid collection container into the waste depository line. The mobile disposal system may further include a backflow preventer connected between the first connector and the water line.

Aspects further include a fluid collection system, including a disposable collection container; and a receiving housing sized to receive the disposable collection container, the receiving housing having: a cavity; a suction source connectable to the disposable collection container; and a piston assembly positioned within the cavity, wherein the piston assembly includes a main piston body and a scraper ring.

The scraper ring may include a peripheral edge that extends above the main piston body and is configured to provide an interference fit with an interior surface of the cavity. The peripheral edge of the scraper ring may be configured to flex against the interior surface of the cavity. The peripheral edge of the scraper ring may extend from the main piston body to a height that enables the peripheral edge to conform to the interior surface of the cavity. The scraper ring may be attached to the main piston body such that the peripheral edge of the scraper ring maintains contact with the interior surface of the cavity when the main piston body is off center. The piston assembly may further include a support structure that supports the scraper ring. The support structure may include ribs formed in the scraper ring and/or ribs formed in the main piston body. The piston assembly may further include a valve assembly communicating between an area adjacent a first side of the piston and an area adjacent a second side of the piston, wherein the scraper ring includes a surface defining openings providing communication between an area between the first side of the piston and a first surface of the scraper ring and an area adjacent a second side of the scraper ring.

The scraper ring may comprise an Ultra High Molecular Weight (UHMW) material. The UHMW material may have a molecular weight of at least one million Daltons. The UHMW material may comprise UHMW polyethylene. The scraper ring may comprises a hydrophobic material.

Aspects may further include a piston stop including a first opening in a cavity wall; a second opening in the cavity wall; and a channel connecting the first opening to the second opening, wherein the first opening is positioned above a desired piston stop height and the second opening is positioned below the desired piston stop height.

The piston stop may further include a valve connected to the channel, wherein the valve has an open position to communicate a pressure differential through the channel between the first opening and the second opening and a closed position to prevent communication of a pressure differential between the first opening and the second opening. The piston stop may further include a third opening in the cavity wall, wherein the channel connects the second opening to the third opening, and wherein the location between the second opening and the third opening is different one of a plurality of desired piston stop positions.

Aspects may further include a fluid collection system, including a disposable collection container; and a receiving housing sized to receive the disposable collection container, the housing having a cavity, a suction source connectable to the disposable collection container, and a filter positioned between the suction source and the cavity, wherein a portion of the filter comprises a hydrophobic material. The filter may comprise a material capable of filtering a gas.

Aspects may further include a fluid collection system, including a disposable collection container having a collection port, and an opening configured to communicate a suction source with an interior of the disposable collection container; and a receiving housing sized to receive the disposable collection container, the housing having a cavity, and a suction source connectable to the opening of the disposable collection container; and a suction instrument having a main body, a porous material attached to the main body, and tubing configured to connect to the collection port.

The main body may a channel configured to communicate vacuum pressure from the suction source to the porous material, wherein the porous material is configured to draw fluid through the porous material into the disposable collection container.

To attain the advantages and other features of aspects of the present invention, as embodied and broadly described herein, one exemplary aspect may provide a fluid collection system having a flexible liner. The fluid collection system may include a container having a top opening, a lid configured to close the top opening, and the flexible liner attached to the lid. The liner may be interposed between the lid and the container when the lid closes the top opening. The liner and the lid may define a substantially sealed interior space therebetween. The lid may include an access port through which the interior space receives fluid. The flexible liner may also be configured to collapse into a substantially collapsed state as the fluid is removed from the interior space.

Additional objects and advantages of aspects of the present invention will be set forth in part in the description which follows, and in part will be obvious from the description, or may be learned by practice thereof. Such objects and advantages may be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE FIGURES

A better understanding of the invention will be had upon reference to the following description in conjunction with the accompanying drawings in which like reference numerals represent like parts.

FIG. 1 is a perspective view of a liquid collection system, in accordance with exemplary aspects of the present invention, illustrating various components.

FIGS. 2-4 are perspective views of a disposable liquid collection container in accordance with exemplary aspects of the present invention.

FIGS. 12A-12E and 13A-13E are schematic illustrations of a liquid collection and disposal sequence, in accordance with aspects of the present invention.

DETAILED DESCRIPTIONS

Figure 5:
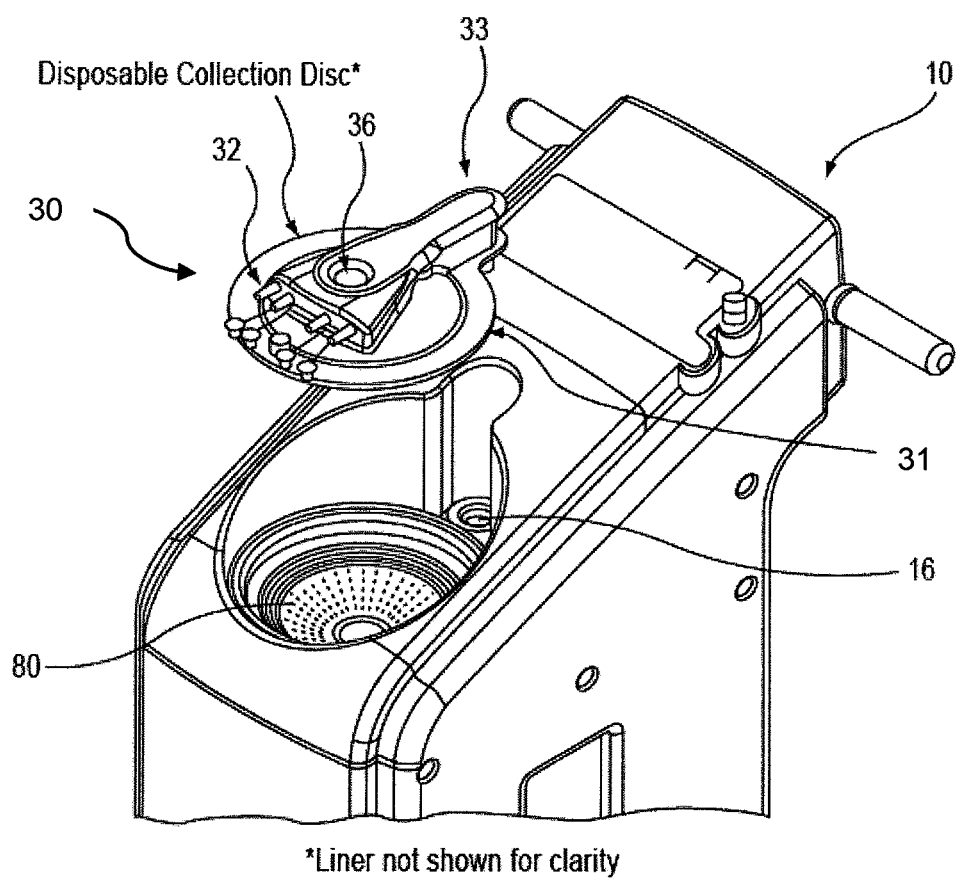
FIG. 5 is a perspective view of a liquid collection system, in accordance with exemplary aspects of the present invention, illustrating various components.

Reference will now be made in detail to aspects of the present invention, examples of which are illustrated in the accompanying drawings. Wherever possible, the same reference numbers will be used throughout the drawings to refer to the same or like parts.

FIGS. 1-5 show a portable fluid collection system 10 (herein also referred to interchangeably as a liquid collection system), according to exemplary aspects of the present invention. The portable fluid collection system may include any of the aspects described in co-pending application Ser. No. 12/076,842 filed on Mar. 24, 2008, titled LIQUID COLLECTION AND DISPOSAL SYSTEM AND RELATED METHODS or application Ser. No. 12/076,841 filed on Mar. 24, 2008, titled FLUID COLLECTION AND DISPOSAL SYSTEM HAVING INTERCHANGEABLE COLLECTION AND OTHER FEATURES AND METHODS RELATING THERETO, the entire contents of both of which are incorporated herein by reference The system 10 includes a main body, also interchangeably referred to herein as a container receiving housing 12, defining a cavity 15 for receiving a fluid collection container 30 (also herein referred to interchangeably as a liquid collection container or a liquid/fluid collection bag) shown in this figure as an exemplary fluid collection bag. The cavity 15 may have various sizes and shapes. A piston 80 (illustrated in FIG. 5) is located in the cavity 15. The system 10 may also include a handle 4 and wheels 19 to facilitate transport of the system 10.

The main body 12 may also include a container holder 18 for receiving a back-up storage container, such as a suction canister.

The term "liquid," as used herein, does not merely refer to a state of matter as defined in the thermodynamic and/or fluid mechanics art. Instead, the term "liquid" also includes any solid particles or gases that may incidentally flow with a liquid medium (e.g., irrigation fluid or blood) or that may be intentionally collected using a liquid medium. For example, when the fluid collection system 10 is used in a surgical procedure, the term "liquid" may refer to a combination of liquid medium (e.g., irrigation fluid, blood, and other bodily liquid from the patient) and any solid particles including, but not limited to, resected tissue removed from the patient's body or harmful particles mixed with smoke or other particulates and/or gases such as may occur in connection with laser, cauterization, and/or other medical procedures. The term "fluid," as used herein may also refer to a liquid medium, solid particles, smoke, gases, particulates, and combinations thereof.

Although not shown in FIG. 1, system 10 may include a vacuum pump for supplying a suction force to the cavity 15 and to the liquid collection bag 30. The system 10 may include appropriate suction conduits (e.g. 14 in FIG. 5) connecting the vacuum pump to the cavity 15 and the liquid collection bag 30. In certain exemplary implementations, instead of, or in addition to, providing the vacuum pump in the main body 12, an alternative suction source may be separately supplied to the system 10. For example, suitable conduits, tubing, fittings, connectors, and/or other hookups may be provided on the main body 12 to allow connection to an external source of vacuum or suction force, such as a wall vacuum in a hospital setting. The availability of an alternative suction source may enable a continuous liquid collection process even when the vacuum pump malfunctions or becomes otherwise unavailable, for example.

The system 10 may include an interface board 13 for enabling control of various features of the system 10. For example, the board 13 may include various buttons 56 for controlling the power supplied to the system 10 and for regulating suction power. The interface board 13 may also include one or more visual or audible indicators that provide various information relating to operational characteristics and/or the status of the system 10, for example when the system is ready for operation, whether the storage bag is filled to an indicated level, whether the filter needs to be replaced, and a vacuum level indicator.

The liquid collection bag 30 may be a disposable unit. As shown in FIGS. 2-4, the collection bag 30 may include a lid 31 and a flexible liner 35 attached to or integrally formed with the lid 31, such that the liner 35 and the lid 31 define a substantially sealed interior space therebetween.

The flexible liner 35 may comprise a sufficiently durable, yet collapsible material, so that, upon applying a negative pressure inside the interior space (e.g., during and/or after fluid is removed from the interior space), the liner 35 can collapse into a smaller volume. The term collapse as used herein, includes and is interchangeably referred to herein as actions in which the sides of the liner 35 fall in, cave in, retract, unextend, compress in, fold, or roll, among other things, and/or which may optionally be forced or otherwise collapsed via operation of a scraping or other squeegee type apparatus.

In some exemplary applications, the liner 35 may additionally include one or more support structures that guide the liner 35 to expand/extend and collapse/retract in a predetermined manner. For example, as shown in FIG. 4, the liner 35 may include a plurality of support rings or a spiral shaped support 37 (e.g., ribs or spirals made of flexible wires), spaced apart from one another along the length of the liner 35, so that the liner 35 may expand and collapse in a bellow-like manner. Alternatively, as seen in FIG. 3, the liner 35 may not include such support rings 37. In either case, in variations the liner 35 extends and retracts along its longitudinal axis. Other variations may include other directions in which the liner 35 extends and retracts.

At least the front portion of the main body 12 may comprise a transparent or translucent material that allows visualization of the liquid being collected in the collection bag 30. In some exemplary implementations, the front portion of the main body 12, the liner 35 and/or the cylindrical body may include graduation marks to indicate the amount of liquid being collected in the collection bag 30.

The lid 31 may include one or more collection ports 32 configured to connect to various medical devices that draw liquid into (or extract liquid from) the collection bag 30. The collection ports 32 may have various different sizes and shapes to accommodate various medical devices that may be used with the system 10. The collection ports 32 may be configured to mate with one or more suction instruments or other devices (interchangeably referred to herein as "suction instruments" or "medical devices") by way of suction tubings for the purpose of drawing liquid into the collection bag 30. The collection ports define one or more fluid passageways via which liquid is transported from the individual (or multiple) suction instruments to the interior space of the collection bag 30. Each of the collection ports 32 may be covered. The cover may be provided via a cap, plug, or flap among others, which closes the respective collection port when not in use. The lid 31 may include suitable valves (e.g., duckbill valves, check valves, spring loaded plungers) to prevent, or at least minimize, liquid dripping while the suction instruments and tubings are disconnected from the collection bag 30 and disposed of in a suitable disposal container (e.g., a red bag). Thus, the lid 31 may reduce the risk of the clinicians' exposure to potentially hazardous materials.

In an exemplary implementation, as shown in FIGS. 1-3, the lid 31 may also include a back-up vacuum port 34 for connecting to a back-up storage container in case the collection bag 30 becomes full or inoperable during a liquid collection process. As illustrated in FIG. 4, the lid 31 may also include a discharge port 38 for evacuating the collected liquid from the collection bag 30, such as after a medical procedure is completed. In an alternative variation, the lid 31 may not have any separate discharge port 38. Instead, one or more of the collection ports 32 may be used to empty the collection bag 30.

During use, the liner 35 is extended to receive fluid, as shown in FIG. 3. As will be explained in detail herein, while the collection bag 30 is being emptied, the liner 35 may collapse again into a state that is substantially similar to its original fully-collapsed state. After an acceptable quantity of liquid is removed from the collection bag 30, it may be removed for disposal in its near-collapsed state.

To begin a liquid collection process, the collection bag 30 is positioned, in its collapsed state, on the mouth portion 11 of the cavity 15, as shown in FIG. 1. An unused, collapsed liquid collection bag may include a holding mechanism such as a strap or band that assists in maintaining the liner portion of the collection bag in a suitable collapsed position. Once positioned in place, the lid 31 of the collection bag 30 may sealingly engage the mouth portion 11 of the cavity 15, so as to form a substantially air-tight enclosure inside the cavity 15 and exterior to the collection bag 30.

FIGS. 6-11 illustrate exemplary aspects of lids for a disposable fluid collection container. In FIGS. 6-11, the lid 31 of fluid collection container 30 defines a vacuum passageway 40 having a U-shaped configuration. The first end 41 communicates with an interior space of the collection bag, and the second end 14 communicates with a vacuum source 16 (in FIG. 5) so as to supply suction force to the interior space of the collection bag. Near the first end 41 of the vacuum passageway 40, the lid 30 includes an overflow valve having a floating ball 44 housed in a cage-like structure 45. Other exemplary lids 31 may include a hydrophilic valve 49 (in FIG. 10-11), such as a porous plastic valve (PPV). As the liquid level in the collection bag 30 reaches the elevational position of the valve, the floating check valve 44, 45 rises to close the vacuum passageways 40 thereby preventing the liquid from flowing into the vacuum pump or the hydrophobic valve 49 blocks the pores of a hydrophobic material, for example using surface tension, and thereby prevents liquid from flowing past the material.

The lids illustrated in FIGS. 4-11 differ from the lids 31 depicted in FIGS. 1-3, in that, among other things, they include a breakable closure member, 39 (in FIG. 9) (e.g., a foil, plastic film, rubber) for closing an evacuation port 36, 38 of the lid. The opening may also include a two-way check valve 42, and a pin 43, for example. FIGS. 5-11 show a variation of the lid in which the exterior of the passageway 40 providing communication between the liquid collection bag 30 and the suction source 16 is configured as a gripping member 33 on the exterior of the disposable lid. This gripping member 33 provides an area removed from the collection ports 32 and from the disposal port 36 by which a user can grip the disposable lid to attach and remove the disposable lid.

Unlike the collection ports 32 shown in FIGS. 1-3, which are used to both collect and remove liquid for the collection bag 30, the evacuation ports, 38 of FIGS. 4 and 36 of FIGS. 5-11 are not used during liquid collection operation and remain sealed by the closure member 39 until the collection bag is to be emptied.

Figure 6:
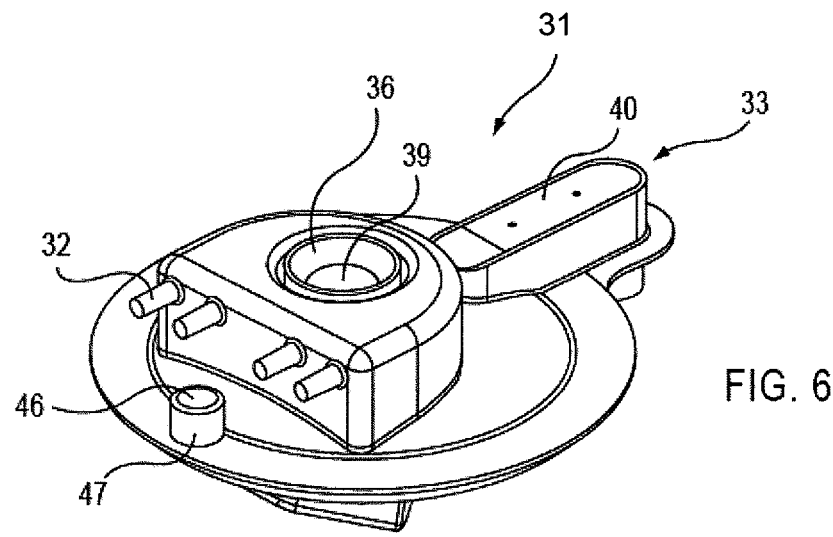
FIGS. 6-11 are perspective views of a lid for a disposable liquid collection container, in accordance with exemplary aspects of the present invention.
Figure 7:
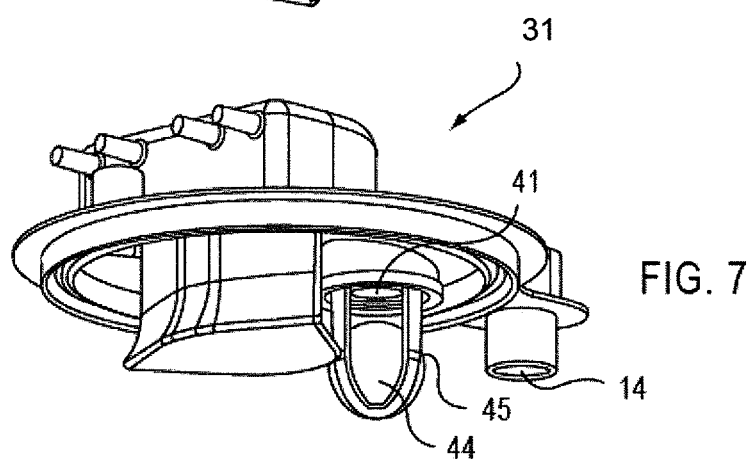
Figure 8:
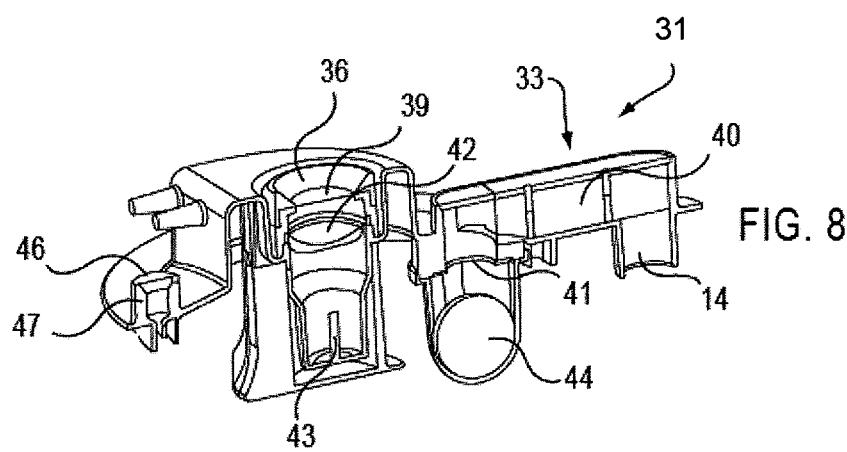
Figure 9:
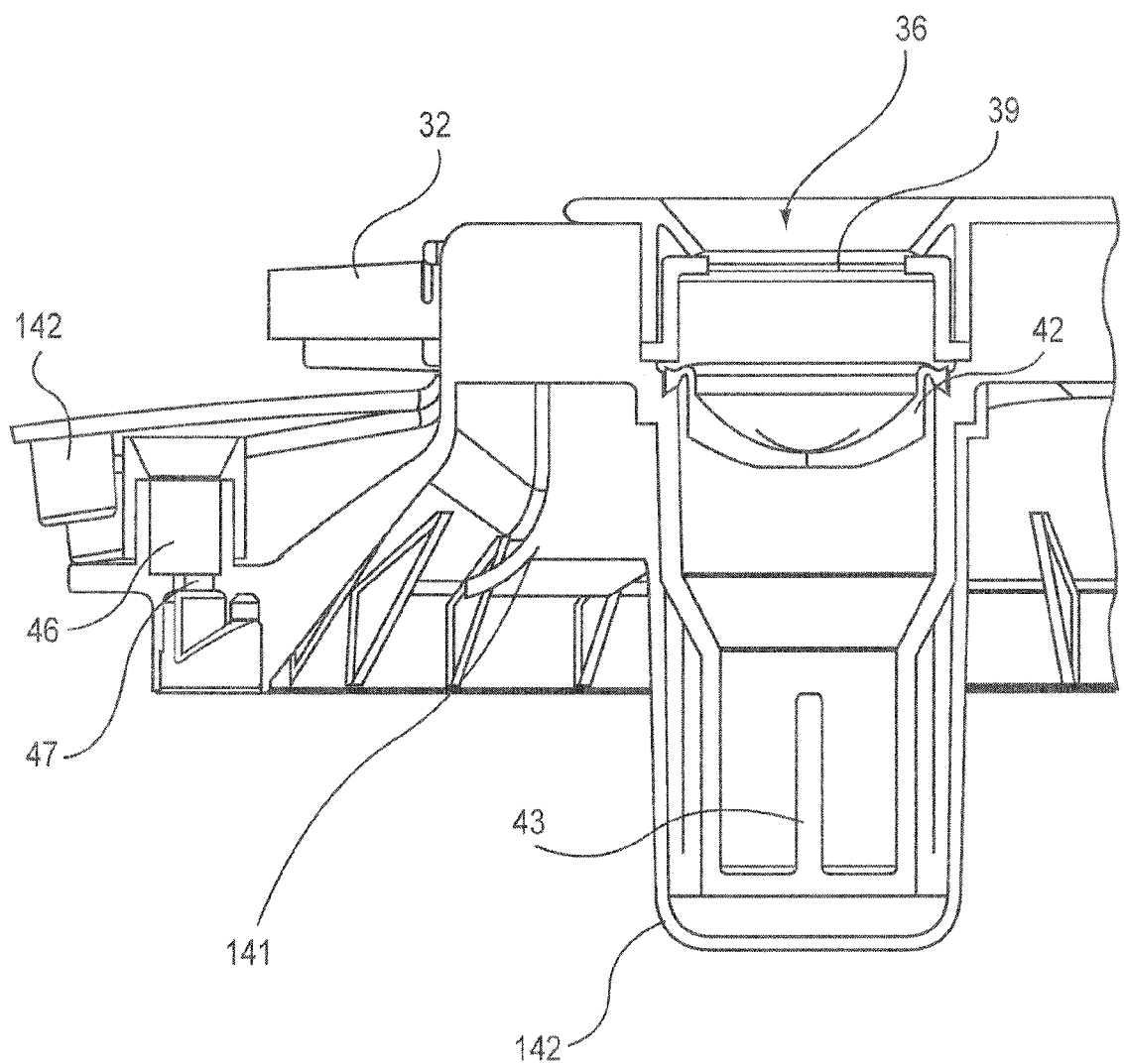
Figure 10:
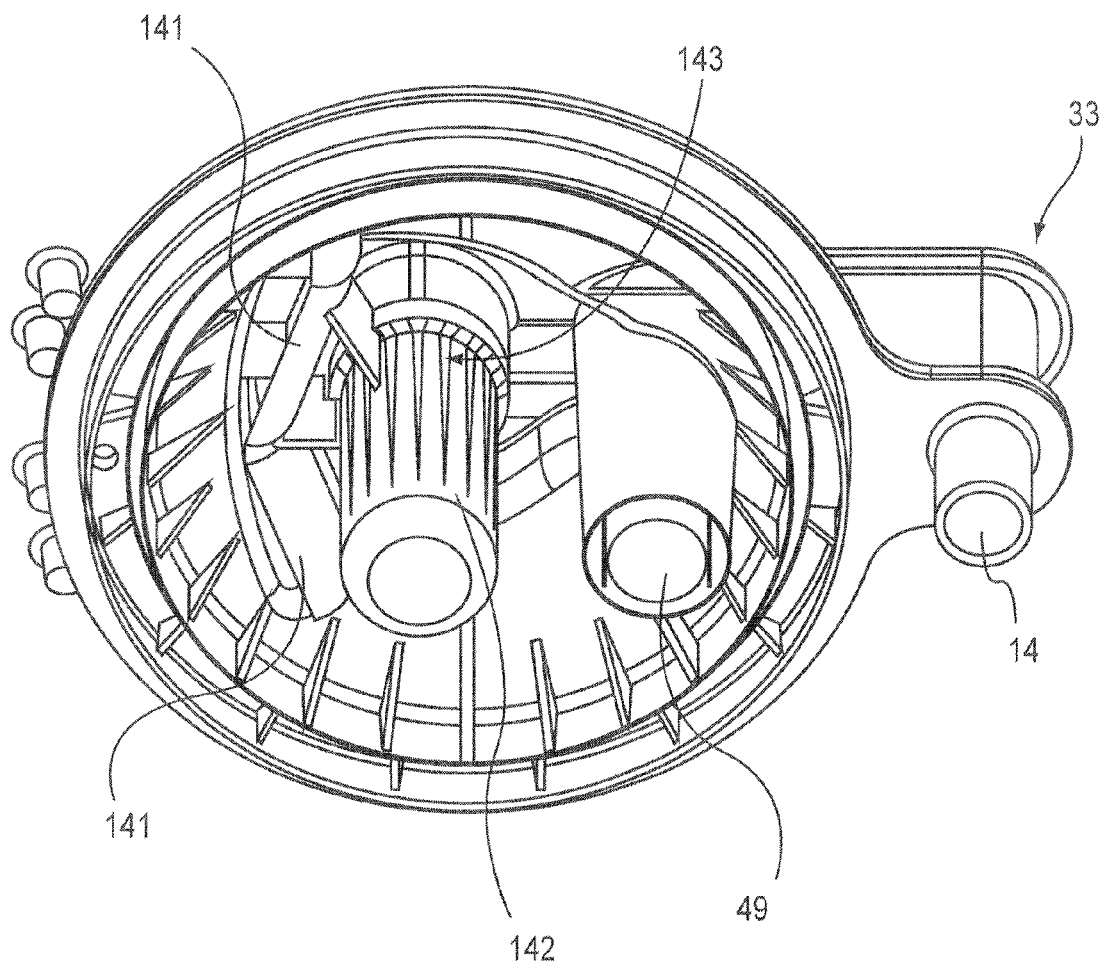
Figure 11:
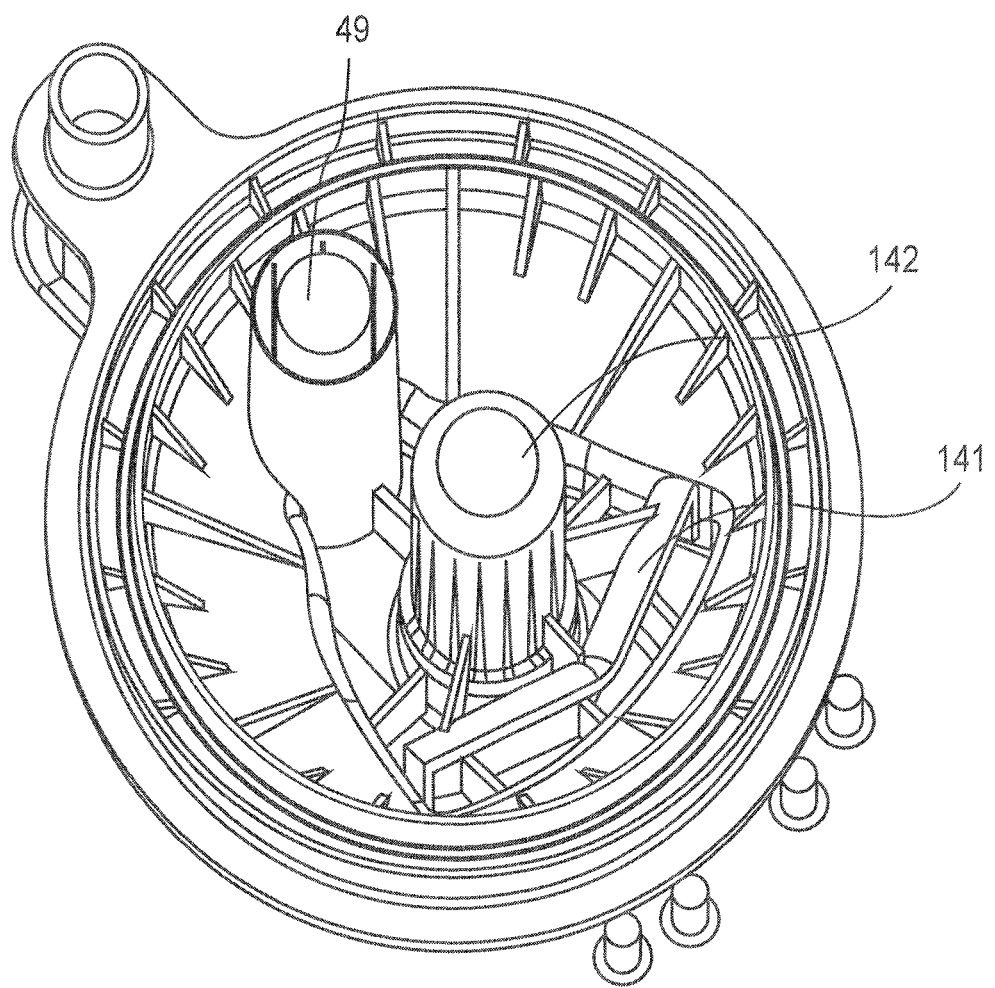

The lid 31 of FIGS. 5-11 also differs from the lids of FIGS. 1-4, in that it forms an interstitial opening 47, as shown in FIGS. 6, 8, and 9 for supplying a source of suction pressure to a space between the rigid receptacle defining a cavity and the collection bag during an evacuation process. The source of suction pressure may be used to equalize the pressures inside and outside of the collection bag during an evacuation process, so that the collection bag may substantially maintain its normal shape during that process. The interstitial opening 47, like the evacuation port 36, may be closed off during the liquid collection process by a breakable closure member 46. Use of the interstitial opening will be explained in further detail in connection with FIGS. 12A-12E and 17.

The lid may include a shelf 141 located between the interior opening of the plurality of ports and the opening communicating with the vacuum source. The shelf 141 extends a sufficient distance to divert collected fluids away from the vacuum source. The shelf may be shaped to direct entering fluid toward the liner walls and away from the shut off valve. The lid may also include a screen 142 surrounding the opening to the evacuation opening. The screen may be shaped to prevent solids collected in the fluid from exiting the collection container during disposal.

The shelf 141 and the screen 142 may also be shaped to prevent the liner from collapsing against the opening to the evacuation port 36, which could, without the present configuration, close off the evacuation port before the contents of the liner are fully evacuated. For example, during evacuation of the contents in the disposable liquid collection container 30, the contents are evacuated via suction through the evacuation port 36. The liner collapses and is drawn toward the evacuation port during this process. If the liner blocks the openings in the screen before all of the contents are removed, the disposal system would be unable to remove the remaining contents. In an aspect, the shelf 141 may be shaped and placed in relation to the screen 142 in a manner that prevents the liner 35 from blocking all of the openings in the screen. For example, the shelf 141 may comprise a portion that extends from the surface of the lid adjacent the screen 142 in order to maintain fluid communication between the evacuation port and the distal portion of the liquid collection container. Thus, at least a partial opening is maintained to the evacuation port, at least in the area between the shelf 141 and the screen 142 to allow continued evacuation of the contents through the openings 143 in the screen 142 and out the evacuation port 36.

Liquid Collection and Disposal Sequence

FIGS. 12A-12E and 13A-13E illustrate exemplary aspects of a liquid collection and disposal sequence. As shown in FIGS. 12A-12E, the system includes a liquid collection bag 30 and a rigid container cavity 15 configured to receive the collection bag 30. The collection bag 30 may include a lid 31 and a collapsible liner 35 attached to the inner surface of the lid 31 to form a substantially sealed interior space therebetween. When the collection bag 30 is placed on the top of the rigid container 15, the lid 31 may substantially seal the opening of the container cavity 15.

As shown in FIGS. 12A-12E, the collection bag 30 may include a suction conduit 233 for connecting the interior space of the collection bag 30 to a suitable suction source (e.g., vacuum pump). The lid 31 may define an access port 220 normally closed by a flexible valve 226, such as an elastic slit valve that is deflected to open the access port 220. The access port 220 may be configured to receive a hose junction 240 and/or an evacuation connector 63. Hose junction 240 may include a ball 249 and pin 224. The lid may also define a second opening that will provide a connection to an evacuation connector.

The container cavity 15 may include a piston 80 (much like a syringe) slidably positioned inside the container 15 to separate the internal space of the container cavity 15 into an upper space 281 and a lower space 289. Aspects of the piston will be described in more detail below. The container cavity 15 may also include a stopper 270 near its bottom, to prevent the piston 80 from descending below the level of the first connection 262. As shown in FIG. 12A, the piston 80 may be initially positioned near the top of the container cavity 15 to receive the collection bag 30.

FIGS. 13A-13E illustrate that cavity 15 may include three vacuum connectors: a first connector 62, a second connector 64, and a third connector 66, each of which may be connected to a vacuum pump. When the collection bag 30 is placed in the cavity 15, the vacuum port 14 of the lid 31 may automatically connect to the first connector 62, so as to supply suction force to the interior space of the collection bag 30. This suction force, in turn, is communicated to the collection ports 32. Each of the vacuum connectors 62, 64, 66 may include a suitable valve to selectively open and close communication with the vacuum pump or to an alternate source of vacuum pressure. In some exemplary variations, the valve associated with the third connector 66 may comprise a three-way valve that can selectively establish fluid communication between the cavity 15 (exterior to the bag 30) and atmosphere.

Figure 12D:
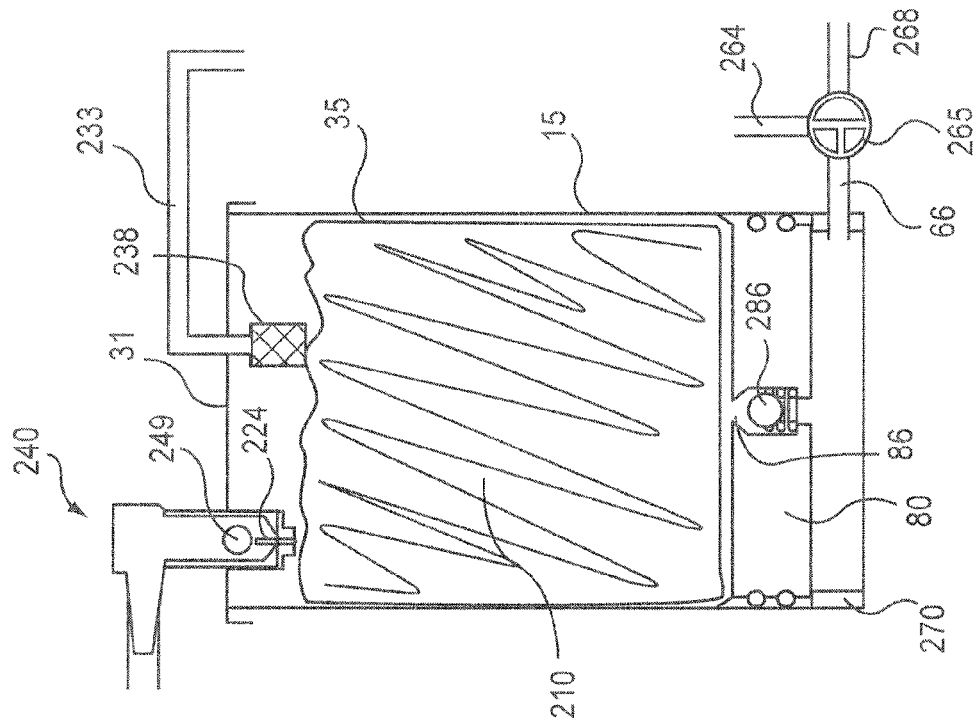
Figure 12C:
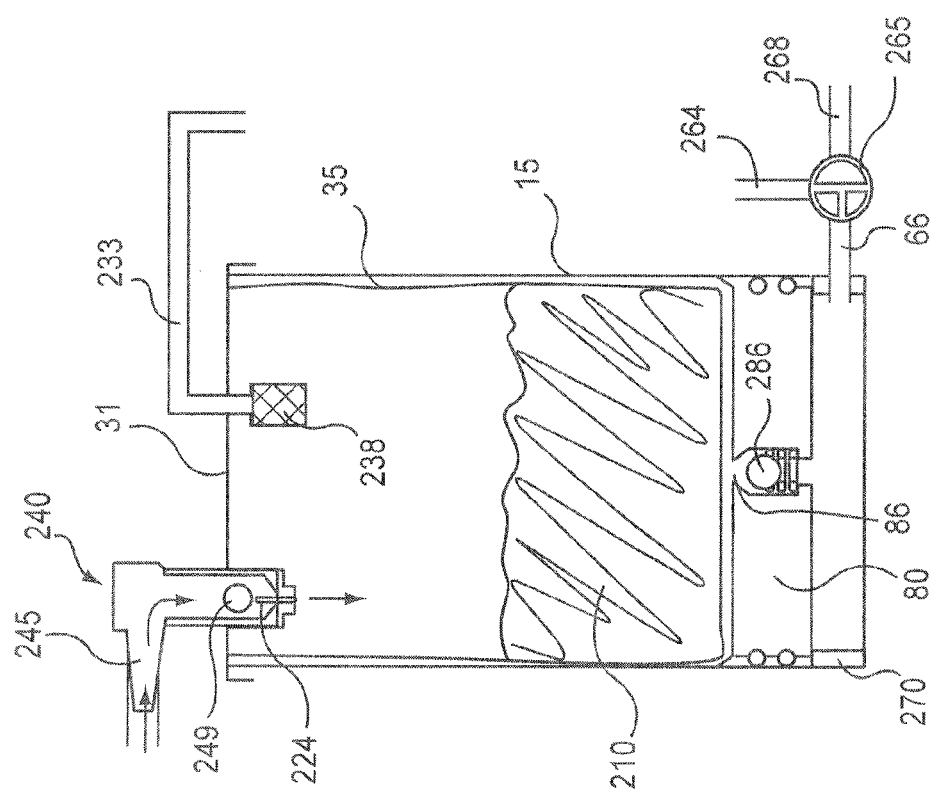

The collection bag 30 may also include various valves associated with the collection ports 32 and the discharge port 38. These valves associated with the collection ports 32, discharge port 38, and vacuum port 14 are schematically shown in FIGS. 13A-13E with circles adjacent the corresponding ports. Solid circles represent closed valves, and open circles represent open valves.

in FIG. 12B, the optional three-way valve 265 may be rotated to align connection 66 with suction source 268 to communicate such pressure within the lower space 289. The suction pressure applied to the lower space 289 draws the piston 80 down into the container cavity 15, which in turn draws the liner 35 into the cavity, thereby expanding the liner into the cavity, as shown in FIGS. 12C and 13B. Although FIG. 13B illustrates the valves associated with the collection ports 32 to be closed, at least one of the valves associated with the collection ports 32 or the discharge ports 38 may be opened to allow air to flow into the collection bag 30. This action draws the liner 35 into the cavity 15 without distorting the shape of the bag and facilitates the downward movement of the piston 80 The suction force applied to the lower space 289 may be greater than the opening pressure of a check valve 286 in the piston 80, so as to open a through-hole 86 and evacuate any excess air in the upper space 281, which may enhance the seal between the lid 31 and the container cavity 15.

However, it may be preferred for the check valve 286 to remain in a closed position during downward movement of the piston 80, so as to further enhance the pressure differential between the lower space 289 and the upper space 281, thereby further facilitating the downward movement of the piston 80 within the cavity.

In an alternative implementation, the liner 35 may not be drawn into the bottom portion of the cavity 15 prior to receiving the liquid. Instead, as the liquid is being collected, the weight of the liquid may cause the liner 35 to expand into the cavity 15.

The second connector 64 provides a connection to the interstitial area between the outside of the liner 35 and the inner wall of the cavity 15. Although the second connector 64 is shown in the figures to be located at a position vertically below the lowermost end of the collection bag 30, as shown in FIGS. 13A-13E, it will be apparent to one of ordinary skill in the art that the second connector 64 may selectively not be opened to atmosphere until the lowermost end of the collection bag 30 is positioned vertically below the elevational position of the second connector 64.

Thereafter, liquid may be drawn into the collection bag 30, as shown in FIGS. 12C and 13C. Communication with a first connector 62 may be opened so as to supply suction force into the interior space of the collection bag 30, and, in turn, via the collection bag 30 to the collection ports 32. During the liquid collection process, the second connector 64 may opened to counterbalance the vacuum force applied to the interior space of the collection bag 30 so that the liner 35 may substantially maintain its normal shape. That is, the second connector opens to a suction force thereby preventing the liner 35 from being drawn back up towards the lid 31 under the influence of the negative pressure within the interior space of the collection bag 30.

Alternatively, a continuously applied suction force in the lower space 289 may cause a check valve 286 in the piston to open, so as to communicate the suction pressure with the upper space 281, which may counterbalance the suction force applied inside the interior space of the collection bag 30 to prevent or reduce collapse or deformation of the liner 35 during the liquid collection process.

The liquid collection process may thereafter end because the medical procedure is completed, for example. This action may also end as a result of suction pressure shutoff, which may occur, for example, when the liquid level rises to the level of the shutoff device 238. For example, when the liquid level reaches the level of the shutoff device 238, the shutoff device 238 may automatically shut off the conduit 233 to stop the liquid collection process, as shown in FIG. 12D.

Figure 12E:
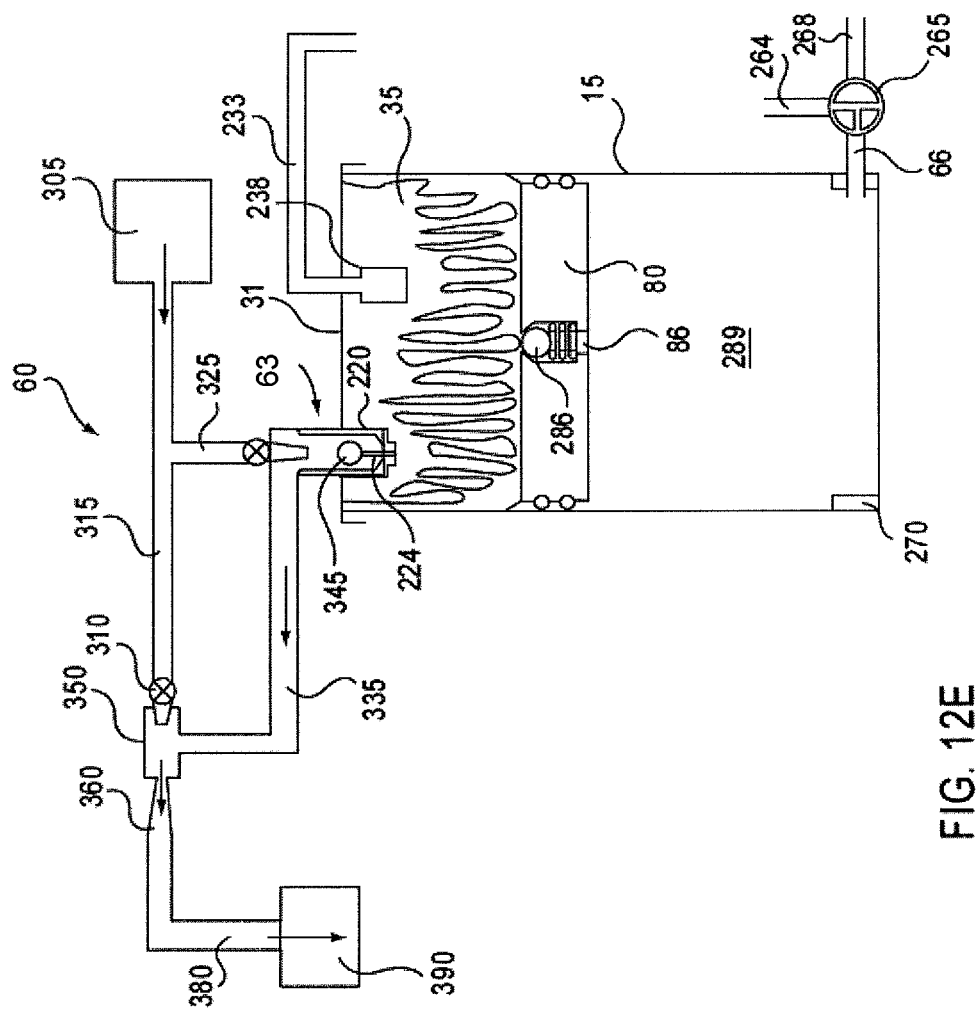
Figure 13:
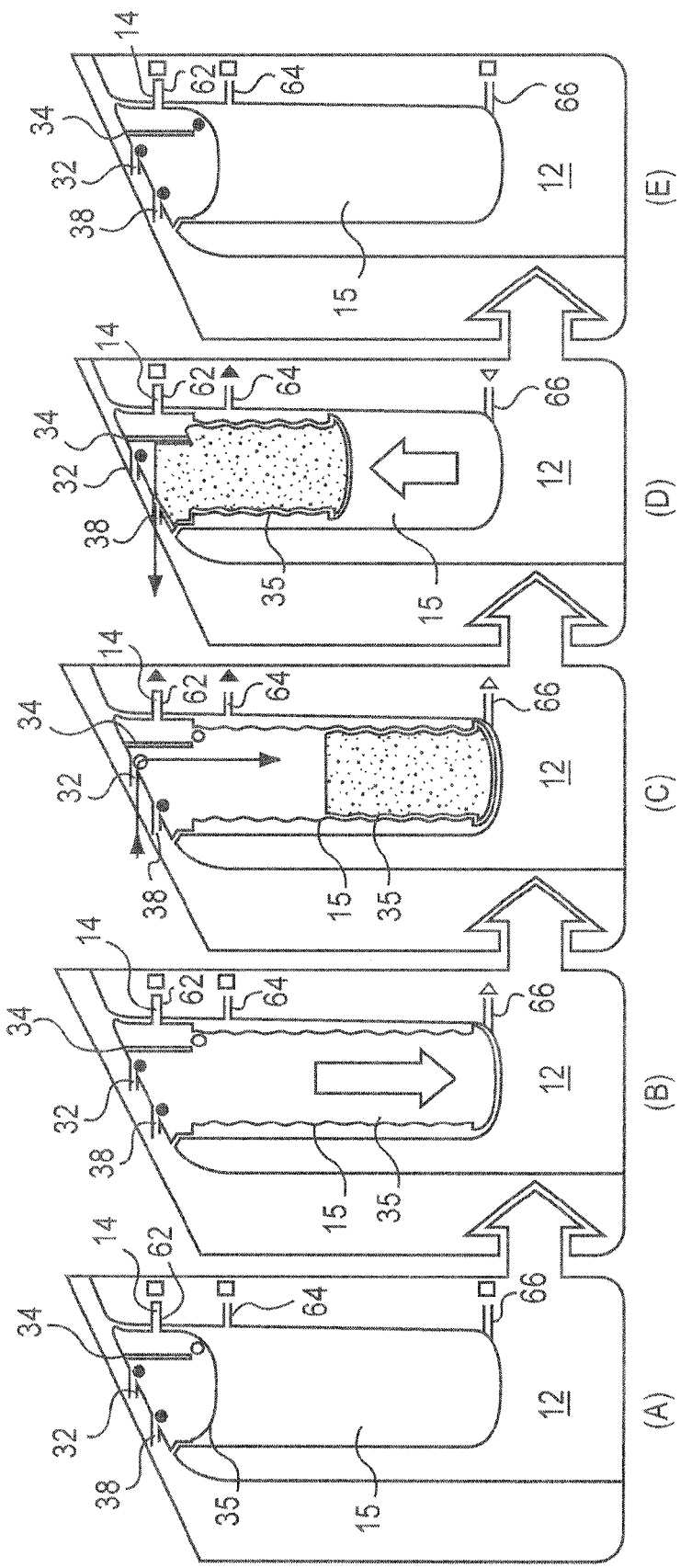

When the collection bag is full and/or otherwise needs to be emptied, the collection system 10 may be transported to a disposal station to extract the collected liquid 210 from the collection bag 30, as illustrated in FIGS. 12E and 13D. The disposal connector 63 may include a drip-free connector valve 345, which is biased to close the distal end of the disposal connector 63. Inserting the disposal connector 63 may cause the connector valve 345 to open, so as to establish fluid communication between the access port 220 and the eductor 350. The disposal connector 63 may also pierce a closure over an evacuator opening in the lid 31. Once the valve associated with the discharge port is opened and connected to a disposal station 60, and the collected contents of the collection bag 30 are evacuated.

The operation of the disposal station will be described in more detail in connection with FIG. 17. FIG. 12E illustrates that the disposal station may include an eductor 350 positioned between a source of water or other rinse fluid 305 and a sanitary sewer 390 to create a pumping force sufficient to draw liquid out of the collection bag 30. In addition, a venturi 360 may be suitably positioned, (e.g., adjacent the eductor 350 in the discharge conduit 380) so as to create a greater pumping force.

To control the collapse geometry of the liner 35 in a manner that does not occlude and prevent the desired discharge liquid flow, check valve 286 may be set in a closed position. The closed position of the check valve 286 prevents air from flowing into the space between the liner 35 and the container cavity 15. Because of the relatively limited air in the space outside of the liner 35, the walls of the liner 35 will not be pulled away from the walls of container cavity 15 and therefore will not close off the passage of liquid within the liner 35.

At this stage, the optional three-way valve 265 may be aligned to communicate the lower space 289 with atmosphere via the first connection 62 and a fourth connection 264, as shown in FIG. 12E. This selection allows the pressure inside the lower space 289 to reach atmospheric pressure during the evacuation process, so as not to interfere with the collapse of the liner 35.

Maintaining the pressure inside the cavity at atmospheric pressure may provide a sufficient pressure difference between the cavity 15 and the interior space of the collection bag, such that the liner 35 may collapse itself toward the lid 31 as the collected liquid is drawn out of the collection bag 30.

For example, maintaining the pressure in the lower space 289 at atmospheric pressure allows the piston 80 to rise during the evacuation process, due to a differential pressure between the upper space 281 (which is subject to a suction pressure) and the lower space 289 (which is open to atmosphere). Because the piston 80 moves up as the liner 35 collapses, the collapse of the liner 35 takes place primarily near the piston 80, and occlusion of the sidewalls of the liner 35 during the evacuation process may be effectively prevented.

Second connector 64 illustrated in FIGS. 13A-13E may be open to vacuum pressure or may be closed off entirely, so as to provide selective regulation of air pressure within the cavity 15 exterior to the collection bag.

Once an acceptable quantity of the liquid is removed from the collection bag 30, and the collection bag 30 is collapsed, the discharge connector 63 is removed from the access port 220. For practical purposes, it may be sufficient for the liner 35 to compact itself enough so as to make subsequent handling and disposal thereof more efficient. After the collected liquid is substantially removed from the collection bag 30, the valves associated with the collection ports 32, the discharge port 38, and the overflow valve are dosed sufficiently to inhibit air from flowing into the interior space of the collection bag 30. Minimizing the amount of air flow into the collection bag 30 allows the collection bag 30 to remain in a substantially collapsed state for disposal. That is, large quantities of air will not be allowed to leak back into the interior space of the bag 30 once the vacuum pressure is removed therefrom.

The collection bag 30 is then removed from the container cavity 15 and placed in a red bag for disposal, for example. A new collection bag may be placed onto the container cavity 15 for the next series of medical procedures.

Disposal Station

Figure 14:
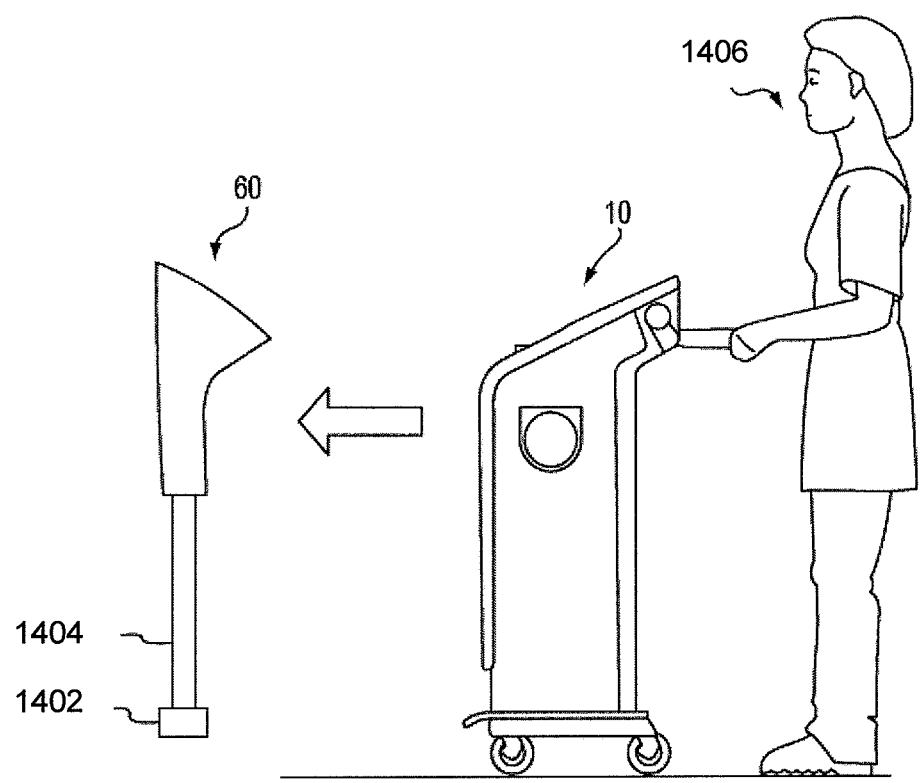
FIG. 14 is a schematic illustration of a liquid disposal system, in accordance with aspects of the present invention.

Once the collection bag 30 is full or otherwise needs to be emptied, the portable liquid collection system 10 may be transported to a disposal station by, for example a clinician 1406 to evacuate the collected liquid from the collection bag 30, as shown in FIG. 14. Although evacuation of the collection bag 30 is not necessary for disposal thereof (e.g., a filled collection bag 30 may be disposed of with liquid still present within the interior space thereof), one aspect of the present invention allows for the evacuation of the collection bag 30 to reduce the volume of red-bag waste produced by disposal thereof.

Figure 16:
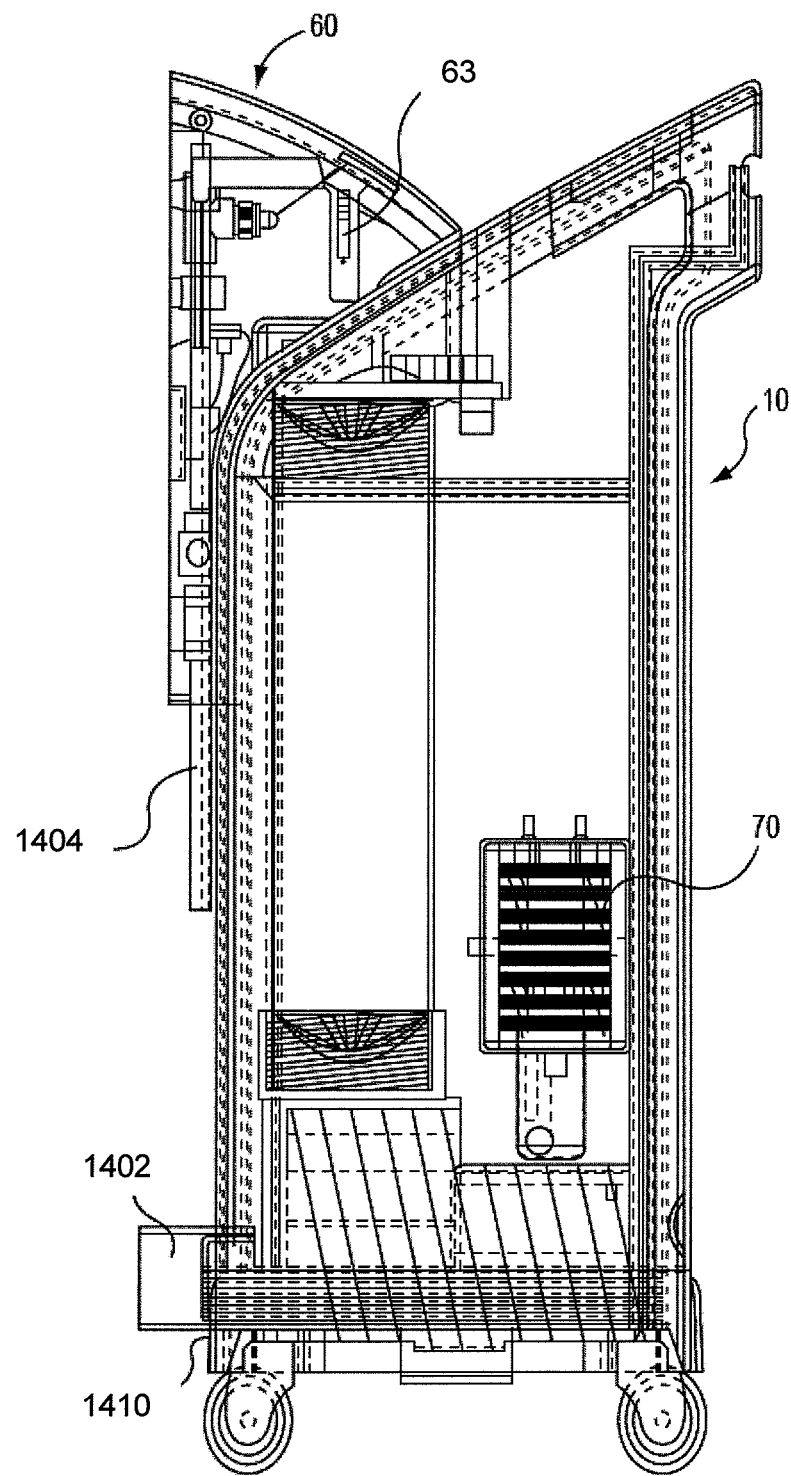
FIG. 16 is a see-through view of a liquid collection and disposal system, in accordance with aspects of the present invention.

In some exemplary variations, the disposal station may comprise a docking station 60 having a fluid connector configured to automatically (or manually) connect to the discharge/evacuation port 38, 36 (for the implementation shown in FIGS. 4, 5), the inlet port 32 (for the variations shown in FIGS. 1-3). FIG. 16 illustrates an exemplary portable liquid collection system docked at a disposal station 60.

Figure 15:
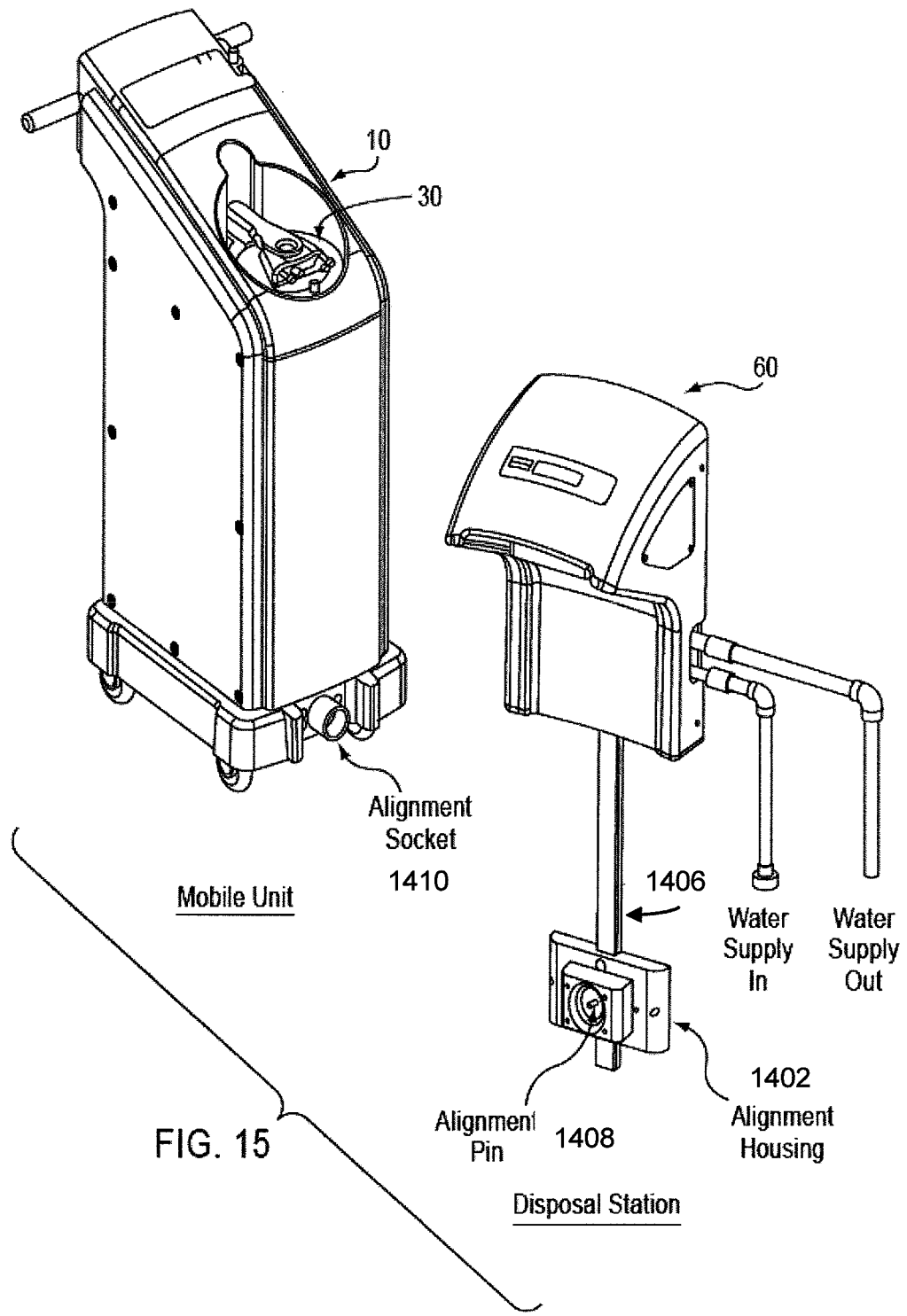
FIG. 15 is a view of another exemplary liquid collection and disposal system, ira accordance with aspects of the present invention.

FIGS. 14 and 15 illustrates that the disposal station 60 may include a reference structure 1404 and a latching member 1402 fixed to the reference structure 1404 for engaging a corresponding latching member 1410 of the liquid collection system 10. Among other things, this approach allows the liquid collection system 10 to be securely and accurately positioned at a predetermined location relative to the disposal station 60. The disposal station may include a connection to a fluid supply, such as water, and a connection to a disposal supply through which collected liquid is evacuated and disposed.

The disposal station may be attached to a fixed location, such as to a wall. Alternatively, the disposal station may be mobile.

Figure 17:
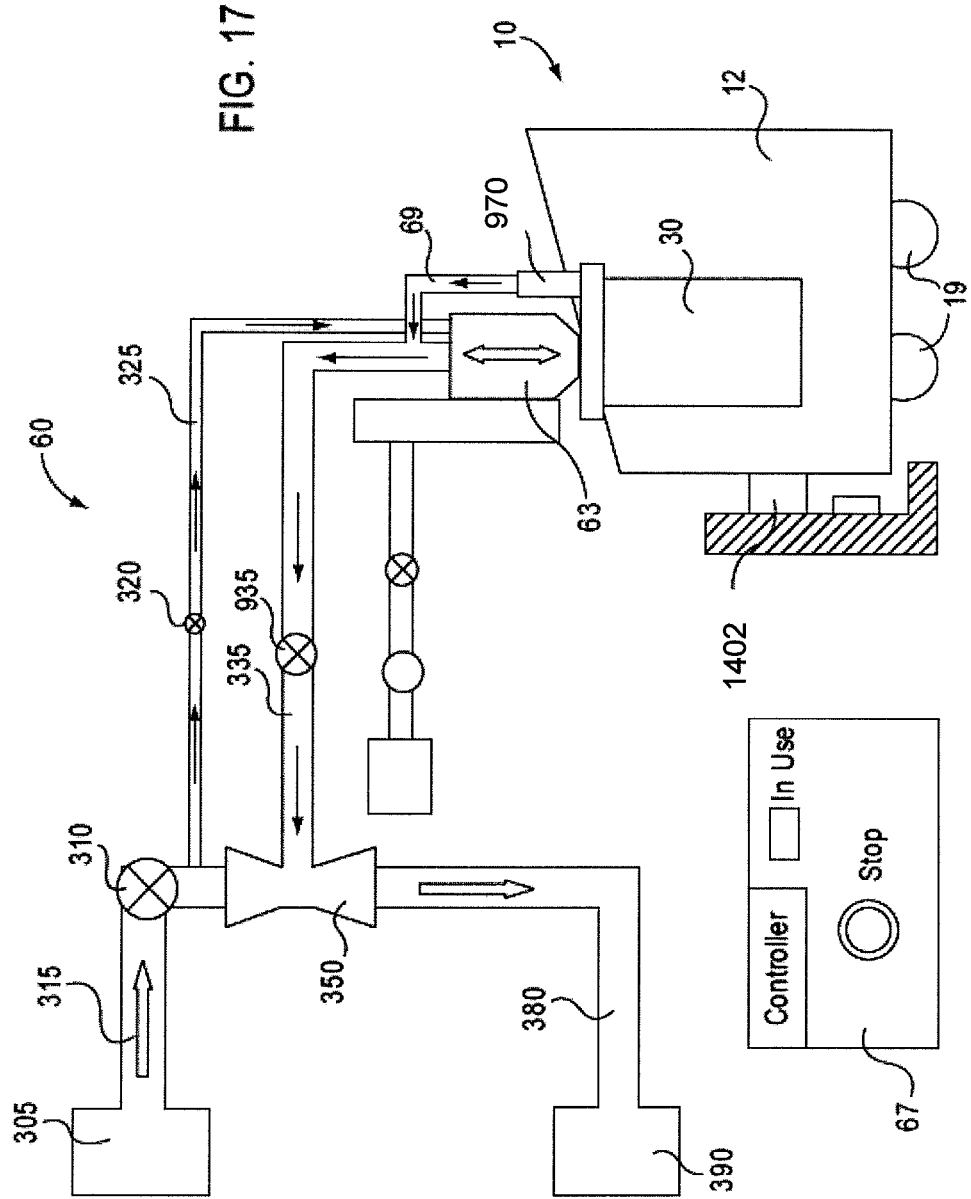
FIG. 17 is a schematic diagram of a liquid disposal station, illustrating various components and their operational characteristics associated with a liquid collection system, in accordance with aspects of the present invention.
Figure 18:
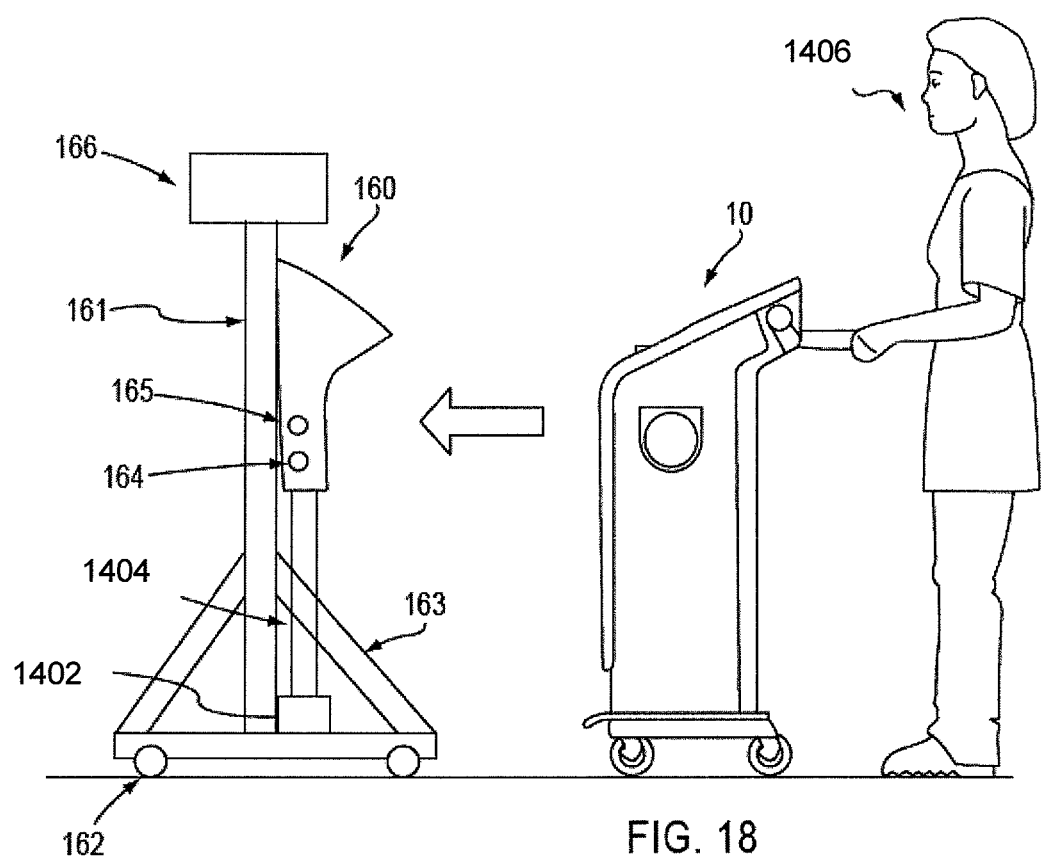
FIG. 18 is a perspective view of a disposal station, in accordance with exemplary aspects of the present invention.

FIG. 18 illustrates a mobile disposal station 160. The mobile disposal station 160 is attached to a mobile frame 161. As illustrated in FIG. 18, the frame may include a relatively low friction component 162 that allows the station to be moved, such as wheels, rollers, skid plates, tracks, etc. The frame 161 may include front and/or ear supports 163. The mobile disposal station has features similar to those discussed in connection with the disposal station of FIGS. 12-17.

The mobile disposal station includes a connection 164 for receiving a water supply line and a connection 165 for receiving a disposal line. The mobile disposal station may include a cord for attaching the disposal station to a power supply.

The mobile station may further include an optional backflow preventer. The backflow preventer may be attached to the mobile frame and connected in series with the water source in order to prevent waste water from flowing back into the clean water supply. For example, the backflow preventer may comprise a one-way valve. Thus, in an aspect, the line of clean water would connect to the backflow preventer 166 and then the backflow preventer 166 would be connected to opening 164 for receiving clean water into the disposal station 160.

To evacuate the collected liquid from the collection hag 30 in some exemplary implementations, the docking station 60 may utilize an eductor of the type described in U.S. Patent Application Publication No. 2005/0183780, entitled "Method and Apparatus for the Disposal of Waste Fluids" and published on Aug. 25, 2005, the entire disclosure of which is incorporated herein by reference. Alternatively or additionally, the disposal station may include a movable connector (not shown) that can be manually connected to the collection bag 30 to evacuate the collected liquid therefrom.

FIG. 17 is a schematic diagram of a liquid disposal station 60, illustrating various components and their operational characteristics associated with a liquid collection system 10. FIG. 17 illustrates that the liquid disposal station 60 may include a user interface 67 for controlling the disposal station 60.

In certain exemplary variations, the process for evacuating liquid from the liquid collection system 10 may be automatically initiated upon engagement of the latching member, although the system may be configured such that an operator is required to manually initiate the evacuation process after the system 10 has been operatively engaged with the disposal station 60.

A liquid collection system 10 is securely positioned in the disposal station, such as via a latch 1408. An evacuation interface 63 and an optional interstitial interface 970 may align with the evacuation port 36 and an interstitial port 47, respectively, of the liquid collection system 10, as shown in FIGS. 6-11. The evacuation interface 63 and the interstitial interface 970 may be connected to a suitable draining system, e.g., 60 from FIG. 12E, for evacuating the liquid from the liquid collection system. The interstitial interface may have an evacuation line 69 that connects to the evacuation source for evacuation interface 63, as illustrated in FIG. 17.

In some exemplary variations, the draining system for the disposal station may include an eductor 350 that provides a source of suction pressure sufficient to draw the collected liquid out of the collection bag of a liquid collection hag 30. In addition to the eductor, other vacuum sources may be used to draw the fluid out of the collection bag. The eductor 350 and the associated flow connections for evacuating the collected liquid may operate similarly to those illustrated in FIGS. 12-13, for example.

The eductor 350 may be positioned between a source of water or other rinse fluid 305 and a sanitary sewer 390, via a water conduit 315 and a discharge conduit 380, respectively. Rinse fluid may consist of water, another wash fluid (e.g. a detergent or other fluid), or a mixture of water and another wash fluid. As noted above, the term "fluid" may refer to a combination of a liquid medium along with solid particles, gases and/or particulates. The water conduit 315 may include a water valve 310, which may be controlled manually or by other control, such as electric switch. The disposal connector 63 may be then connected to the eductor 350 via an evacuation conduit 335.

Opening the water valve 310 causes the water from the source of water 305 to flow into the eductor 350 to create a pumping force in the eductor 350. This pumping force causes the liner 35 to collapse and then liquid collected in the collection bag 30 to flow into the eductor 350 and then into the sanitary sewer 390 via the discharge conduit 380.

The disposal station 60 may include a pipe conduit 325 that branches from the water conduit 315 to supply cleaning water or other cleaning substance to the disposal connector or evacuation hose junction 63. The pipe conduit 325 may include a valve 320 (e.g., an electric solenoid valve, or a ball valve) that controls the water flow into the interior of the disposal connector 63.

After liquid is removed from a collection bag, clean water or other substance from the pipe conduit 325 may flow into the interior of the evacuation hose junction and around a valve, flushing the entire surface of the valve. This can be cycled on and off one or more times to rinse or flush it off as a preventive maintenance for the evacuation interface. The cleaning operation may be performed before the evacuation interface is removed from the evacuation port so that cleaning substance may flow to the exterior of the evacuation interface and then be suctioned back through the interior of the evacuation interface, thereby flushing any residual fluid or other particles from the components of the interior of the interface.

According to one aspect of the present invention, conduit 325 (which supplies cleaning water to the disposal connector 63) is in fluid communication with discharge conduit 380, which is used to "charge" the eductor 350, and to thereby suction fluid from the collection bag 30 (as described above). In this manner, cleaning fluid will not be supplied to the disposal connection 63 unless the eductor is suctioning fluid from the collection bag 30, thereby preventing unintended flooding of the collection bag 30 with cleaning water.

The interstitial port 47 of the lid 31 may be in fluid communication with an interstitial space within a cavity external to a liquid collection bag, and the supply of a suction force to the interstitial space may equalize the pressure inside and outside of the collection bag during an evacuation process, so that the collection bag may remain substantially uncollapsed during the evacuation process. Providing the interstitial port 47 in the lid 31 may eliminate the need for a power supply in the liquid collection system 10 during the evacuation process, which may otherwise be required to supply suction source to the interstitial space, similarly to the function of the second vacuum connector 64 in FIGS. 13A-13E.

In other variations, a seal between the lid of the liquid collection bag and the top 11 of cavity 15 and at least seal between the piston and the inner walls of the cavity maintain vacuum pressure on the outside of the collection bag by preventing air from entering the interstitial space so that the sides of the bag do not collapse during an evacuation process. By limiting air flow into the interstitial space between the bag and the inner walls of the cavity, communication between a suction source and the interstitial space is unnecessary/optional during an evacuation process. In addition, air flow into the interstitial space may be controlled via a check valve in the piston. These seals assist in equalizing the pressure inside and outside of the collection bag during a collection process and continue to maintain that pressure up through at least part of an evacuation process.

In exemplary variations, air flow may be allowed into the interstitial space near the end of an evacuation process in order to fully collapse the liquid collection bag 30 by allowing communication between the atmosphere and interstitial space.

According to certain exemplary implementations, the disposal station may include a linear slide, along which the evacuation interface 63 and the interstitial hose junction may slidably engage the evacuation port 36, 38 and the interstitial port 47, respectively. Movement of the evacuation interface 63 and the interstitial interface relative to the linear slide 63 may be controlled, for example, pneumatically by a compressor or other suitable movement mechanism, a flow control pilot, and a flow control valve (e.g., a two-way solenoid valve).

The evacuation port 36, 38 and the interstitial port 47 may remain closed by breakable closure members, e.g., 39, 46, during the liquid collection process. These breakable closure members may be pierced or broken when the evacuation interface 63 and the interstitial interface 970 engage the evacuation port and the interstitial port.

As shown in FIG. 12E, the evacuation interface 63 may include a normally-closed valve (e.g., a duckbill valve, a check valve, a spring-loaded valve, a poppet valve) to open and close its passageway. In the exemplary variation, the valve 345 includes a ball biased against a distal end of the hose junction. The valve may be opened from its normally-closed position by an actuation rod or pin positioned inside the evacuation port, for example.

Piston

Figure 19:
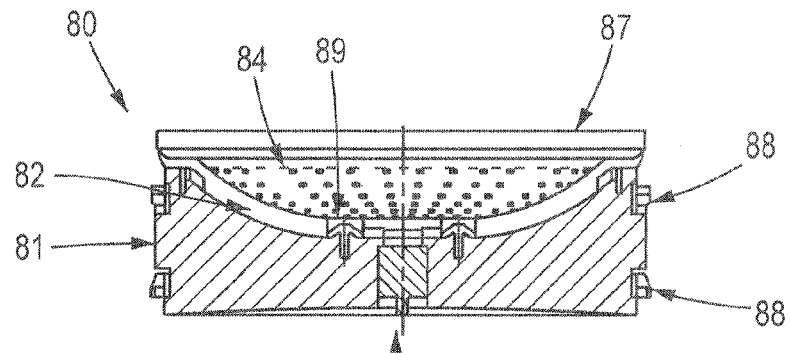
FIGS. 19-21 illustrate an exemplary piston, in accordance with aspects of the present invention.
Figure 20:
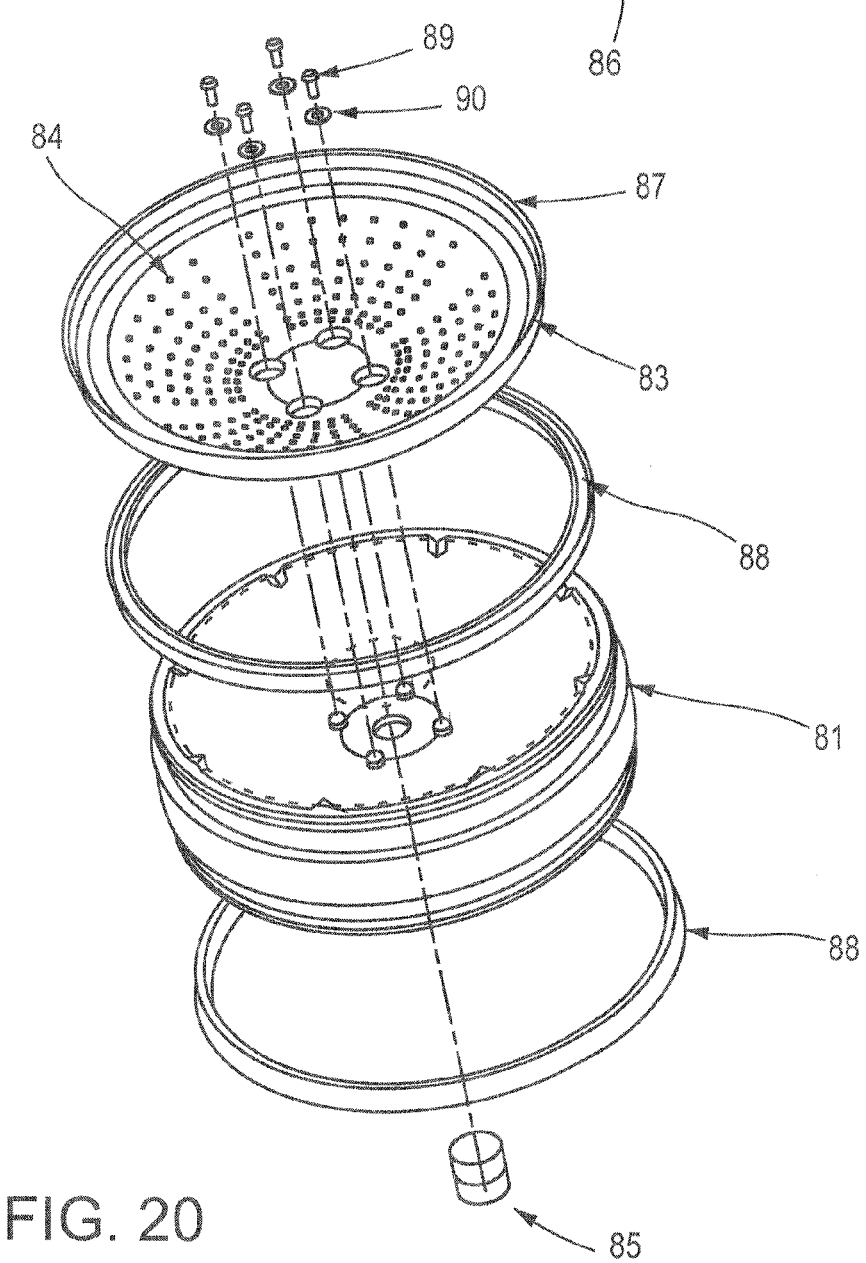
Figure 21:
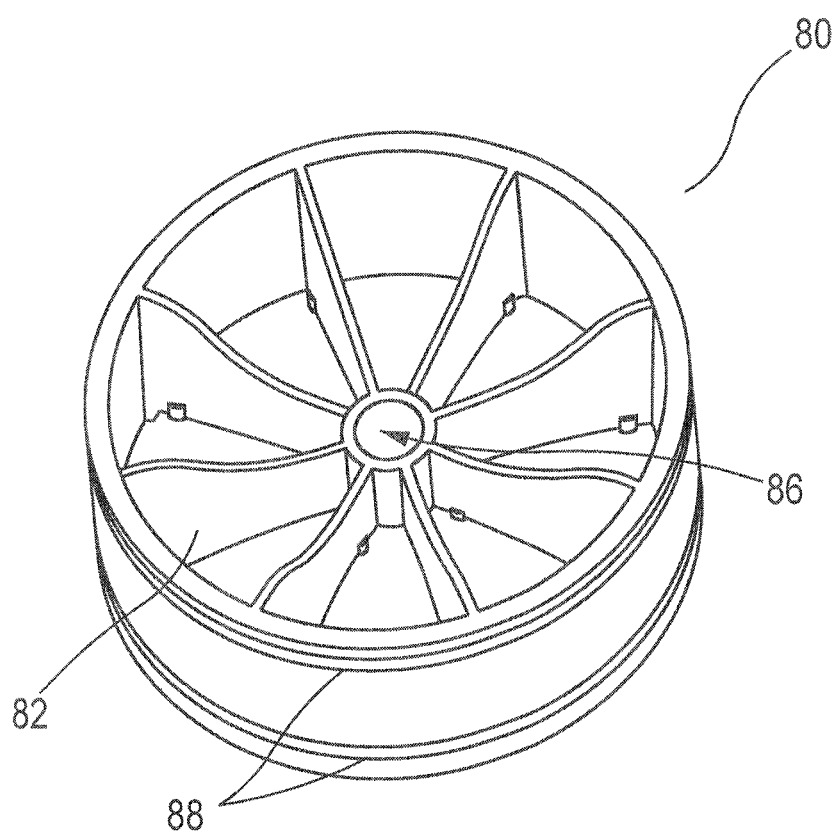

FIGS. 19-21 illustrate an exemplary piston 80. The piston 80 may include a main body 81 shaped to fit a cross section of the interior of the cavity 15 in the liquid collection system 10. In one aspect, the main body may have at least one seal 88 configured to maintain a seal between the piston 80 and the interior wall of the cavity 15. In another aspect, to provide additional sealing capability, the main body 81 may include a plurality of seals 88, such as the two illustrated. Each seal may include, for example, an O-ring attached to the outer peripheral edge of the main body. The O-ring may include a material or be coated with a material to enhance lubricity and/or durability. The piston 80 may also include a through hole 86 and a valve assembly 85, as discussed in connection with FIGS. 12A-12E.

The piston 80 may also include a scraper ring 83 configured to prevent a liner 35 of a liquid collection bag from being pinched between the inner wall of the cavity 15 and the piston 80. The scraper ring includes a plurality of openings 84 that allow air flow through the scraper ring 83 and an outer peripheral edge 87 that extends above the main body of the piston 80. When inserted into the cavity 15, the peripheral edge 87 of the scraper ring 83 may have a tight, interference fit with the interior wall of the cavity 15. The outer peripheral edge 87 of the scraper ring may be thin so that it does not allow a liner 35 from a liquid collection bag 30 to become caught between the scraper ring and the inner wall of the system. The edge of the scraper ring may also be thin enough that it can be flexed to contact the entire surface area of the inner wall of the cavity 15. As the peripheral edge of the scraper ring is thin, the peripheral edge may also comprise a material that is stiff enough to maintain a tight interference fit and to maintain the shape of the edge as it moves against the cavity wall. Additionally, the peripheral edge of the scraper ring may extend above the main body of the piston to allow a thin edge to maintain compression against the inner cavity wall. This enables the scraper ring to move the bag away from the inner wall of the cavity 15 without catching the bag between the inner cavity wall and the piston.

While the scraper ring 83 has an interference fit with the inner wall of the cavity 15, the scraper ring 83 may be attached to the main body 81 of the piston 80 in a relatively loose manner. For example, the piston assembly may further include a movable connector that connects the scraper ring and the main piston body, wherein the movable connector allows the scraper ring to move with respect to the main piston body. This relatively loose connection with the main body 81 enables the scraper ring 83 to self center against the inner wall of the cavity even when the piston is not centered. The scraper ring may be attached to the main body 81 of the piston, for example, using a bolt such as a shoulder bolt. FIG. 20 illustrates an exemplary variation of the piston 80 having four bolts 89 and four washers 90 attaching the scraper ring to the main body 81 of the piston.

As the piston 80 moves during liquid collection and disposal, the main body 81 of the piston may tip, e.g. become angularly offset, relative to the inner wall of the cavity 15. As the piston becomes cocked, a loose connection between the main body 81 of the piston and the scraper ring 83 allows the scraper ring to maintain its flat position, e.g. angular alignment, and to maintain contact between its outer peripheral edge 87 and the inner wall of the cavity 15. Thus, based on the described configuration, no gap forms between the scraper ring 83 and the inner wall of the cavity such that the liner 35 may be caught.

The scraper ring 83 may include a material having an Ultra High Molecular Weight (UHMW). The molecular weight may be above a million Daltons. The high molecular weight provides a low coefficient of friction and high wear resistance for the scraper ring 83. The lower coefficient of friction causes the scraper ring to have a characteristic similar to significant lubrication. Also, the scraper ring may be formed from a material that is flexible enough to press against the inner wall of the cavity 15 in an interference fit, yet also rigid and stiff. The scraper ring may also include a material that is hydrophobic so that the scraper ring does not swell if it comes in contact with liquid. For example, the scraper ring may comprise a material such as UHMW polyethylene.

The piston may include a support structure to support the surface of the scraper ring 83 adjacent to the main body 81. The support structure may include ribs 82 in at least one of the scraper ring 83, as in FIG. 19, or ribs 82 in the main body 81 of the piston, as in 21, adjacent to the scraper ring. The ribs 82 may be configured to allow for air flow through the openings 84 in the scraper ring by supporting the scraper ring above the main body 81.

This allows, for example, vacuum pressure from air released through the piston check valve 85 to be distributed across the openings in the scraper ring to the bottom surface of liner 35.

In addition to ribs, the thickness of the scraper ring may be increased in order to provide enough support for the scraper ring to maintain its shape. However, the edge of the scraper ring should be thin enough that it does not allow the liner 35 to be caught between the inner wall of cavity 15 and the edge 87 of the scraper ring.

In addition, the scraper ring may be maintained at a flat position, thereby preventing gaps between the inner wall of the cavity 15 and the peripheral edge 87 of the scraper ring even when the scraper ring is firmly attached to the main body 81 of the piston, by increasing the thickness of the main body 81. For example, the thickness of the piston may be increased to about the same amount as the diameter of the piston. Increasing the thickness of the piston 80 prevents the piston from tipping relative to the inner wall of the cavity 15.

Piston Stop Feature

Figure 22:
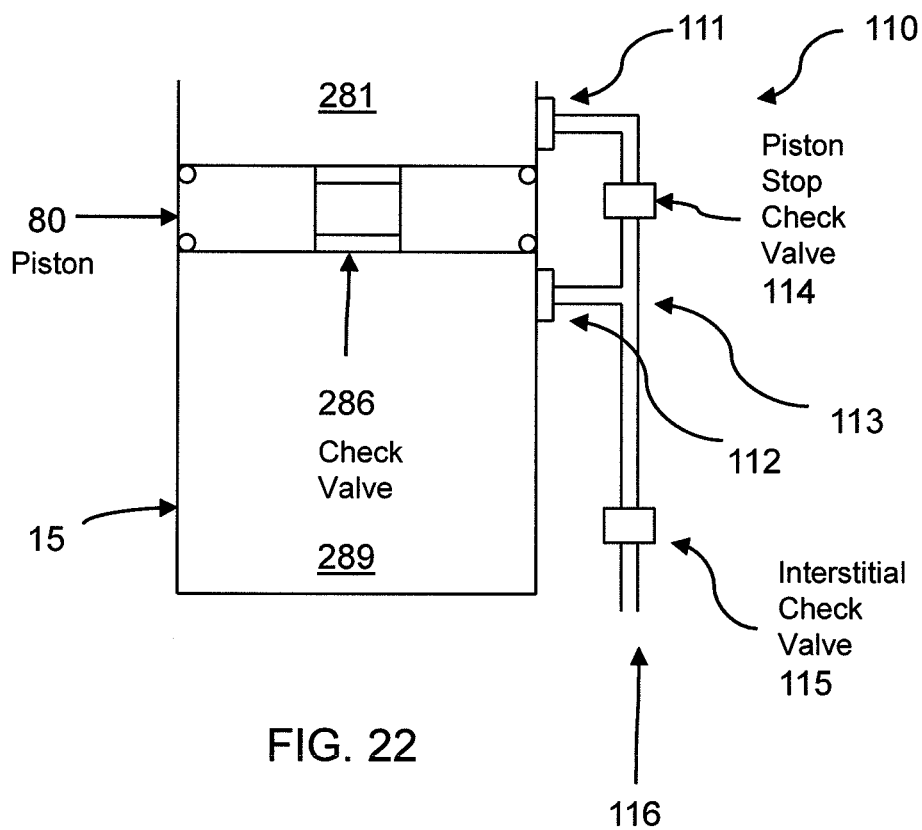
FIGS. 22-25 illustrate an exemplary piston stop feature, in accordance with aspects of the present invention.

The collection system 10 may further include a piston stop feature. This may include a stopper on the interior of the cavity 15 that physically stops the piston from rising, similar to the stop 270 illustrated in FIGS. 12A-12E. In order to prevent damage to the piston and/or the liner becoming caught between the stopper and the piston 80, the housing 12 may include a piston stop feature that will function by regulating the pressure between the space 281 above the piston and the space 289 below the piston. FIG. 22 illustrates an exemplary piston stop feature.

For example, during an evacuation of collected contents in the liquid disposal bag, there may be a positive pressure under the piston. The portion 289 of the cavity under the piston may be open to the atmosphere, while the upper portion 281 is subject to a lower pressure. Thus, the piston is drawn toward the upper portion of the cavity and assists in the evacuation of the contents of the liquid collection bag. In this aspect, the piston stop 110 has a structure that allows the area 281 above the piston to communicate with the area 289 below the piston, thereby regulating the pressure between them. Such a communication structure stops the movement of the piston because there is no pressure differential between the portions of the cavity on either side of the piston. For example, in an aspect, the piston stop may include an opening 111 to the area above the piston and an opening 112 to the area below the piston. These openings are connected via a channel 113. The channel 113 may further include a valve 114 that may be opened or closed. If the valve 114 is open, movement of the piston 80 will stop. However, if the valve 114 is closed, the piston 80 will continue to move because the pressure difference will not be regulated for the portions of the cavity above 281 and below 289 the piston.

The piston stop feature may be configured at any height of the cavity, depending on the desired stopping position of the piston. The piston stop feature may be used to stop the movement of the piston in either direction. The interstitial opening (e.g. 64 in FIG. 13) to the cavity may be the same as one of the openings 111, 112 for the piston stop 110. The connection to the interstitial opening 116 may include a check valve 115 that allows the interstitial pressure to be regulated separate from the piston stop feature 110.

Figure 23:
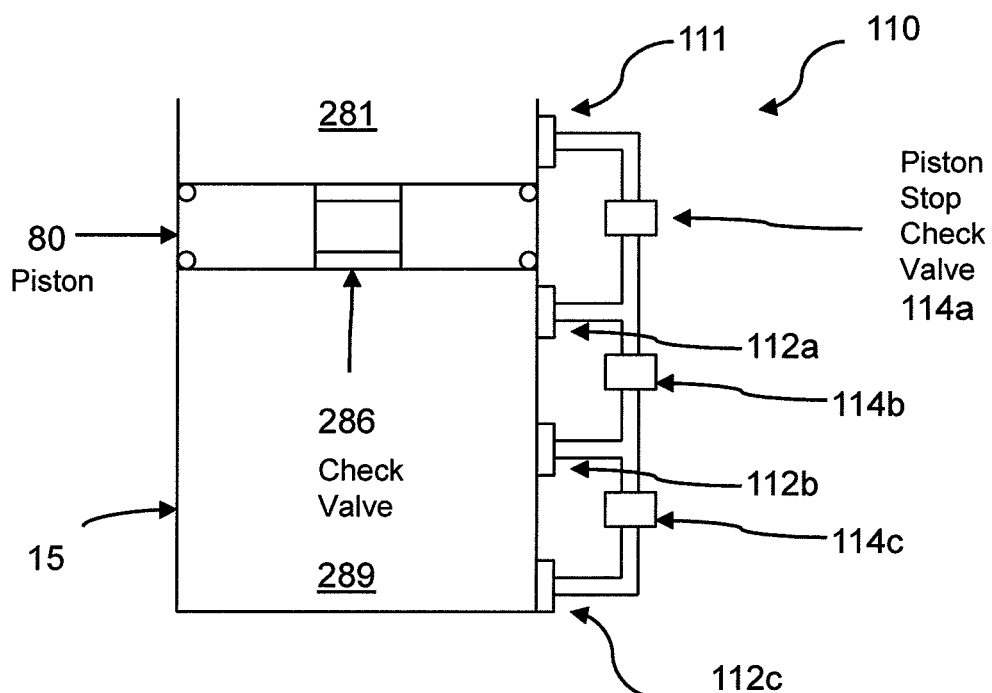
Figure 24:
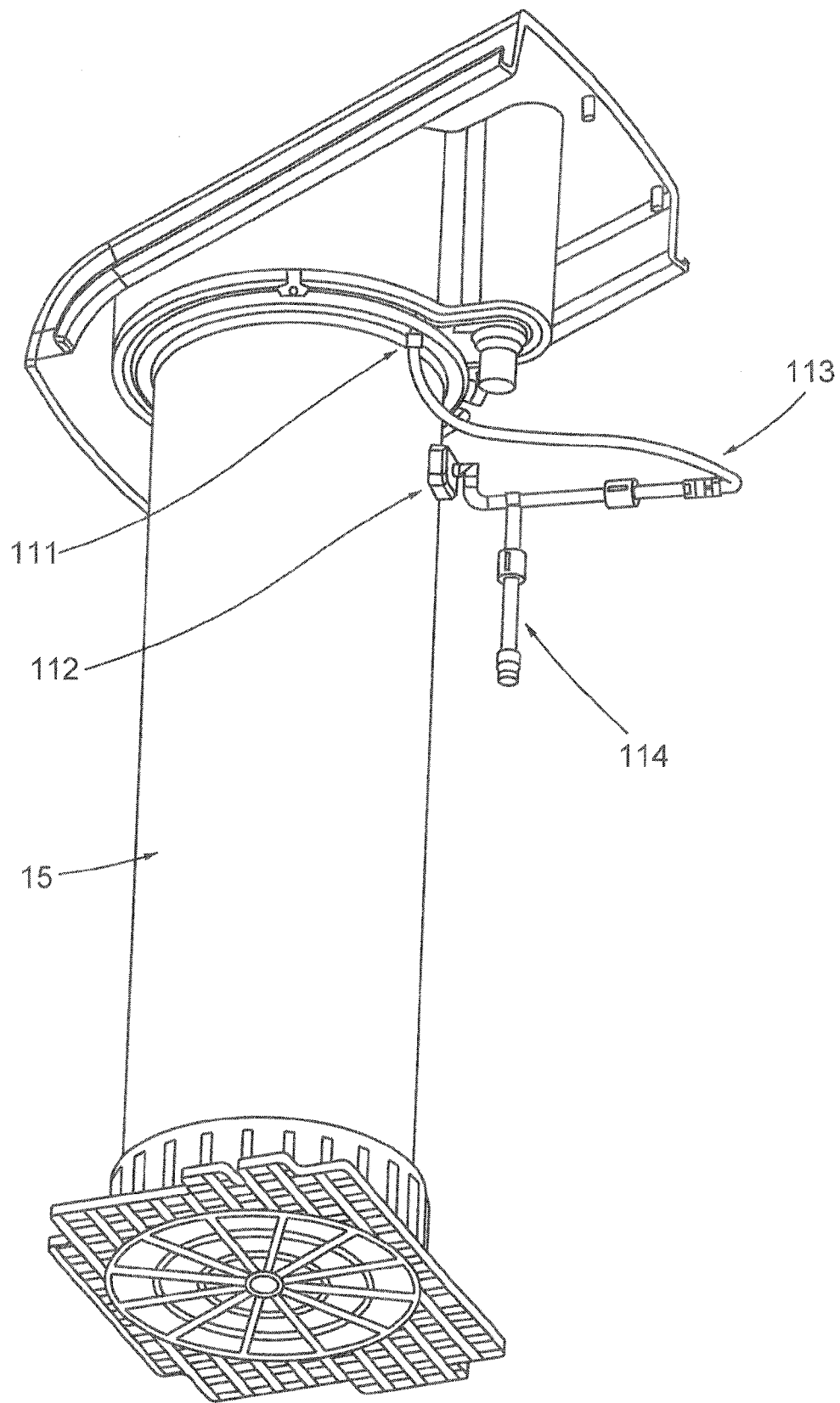
Figure 25:
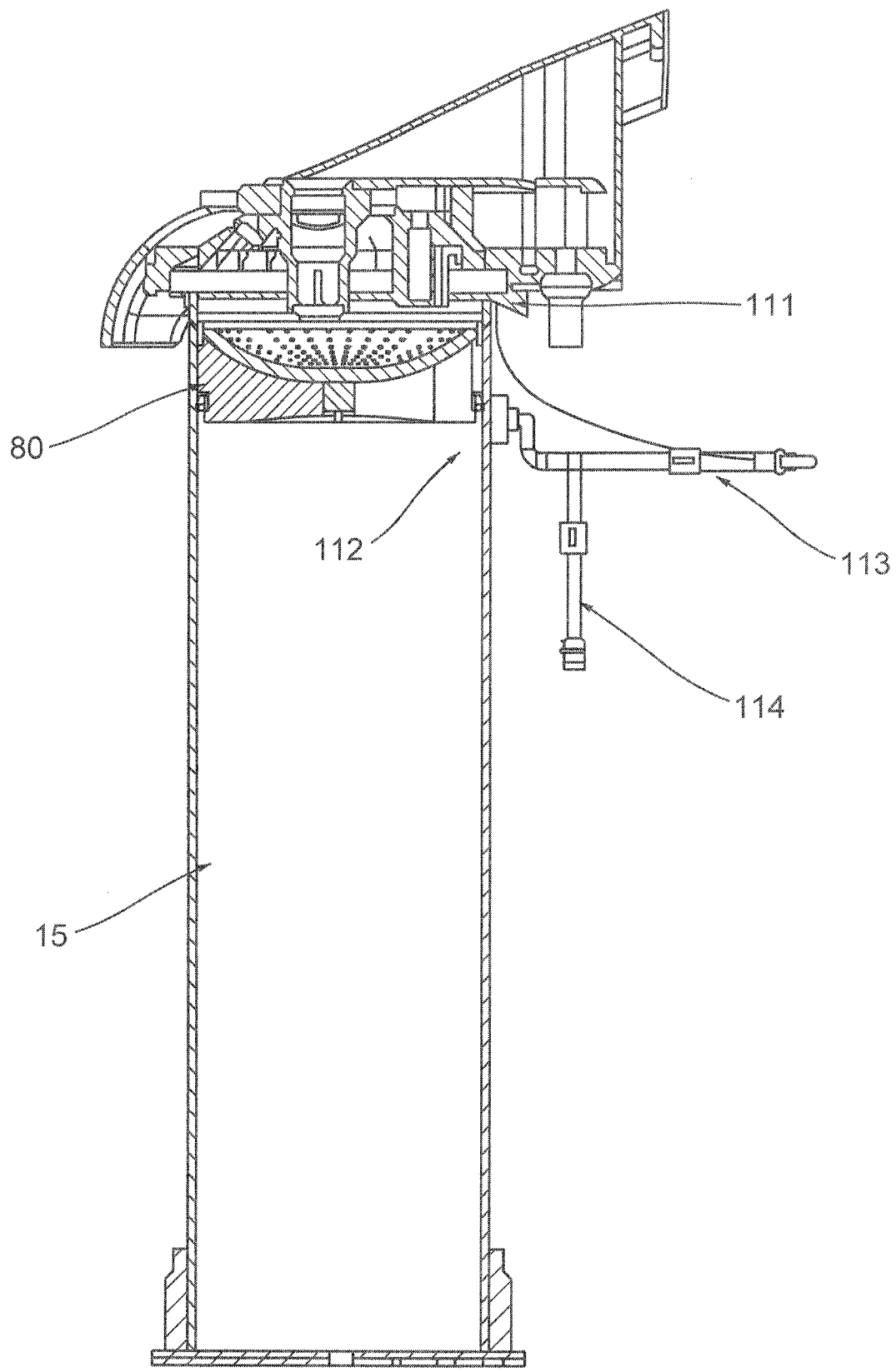

Although the use of the stop feature was described above for evacuation, the piston stop 110 may also be used to stop a downward movement of the piston during collection. In addition, the stop feature may include any number of openings 111, 112a, 112b, 112c, etc. to allow the piston to be stopped at multiple positions, as illustrated in FIG. 23. The piston may be stopped at a position based on which valve 114a, 114b, 114e, etc. is open, which allows the movement of the piston to be stopped at a predetermined level. For example, the piston stop may be set to stop the movement of the piston at a level corresponding to the collection of a plurality of volumes of fluid, e.g. 1 liter, 2 liters, 4 liters, 8 liters, etc. The check valves 114a, 114b, 114c between any two of openings 111, 112a, 112b, 112c may be opened to cause the piston to stop. The cheek valves 114a, 114b, 114e may be closed to allow the piston to continue its movement. The interstitial opening may coincide with one of the openings illustrated in FIG. 23 as illustrated in FIG. 22. FIGS. 24 and 25 further illustrate exemplary aspects of the piston stop 110.

Filter

Figure 26:
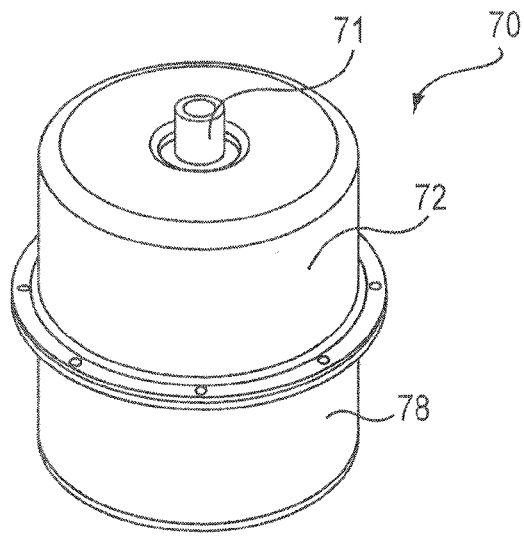
FIGS. 26, 27A-27B, and 28 illustrate an exemplary filter, in accordance with aspects of the present invention.
Figure 27A:
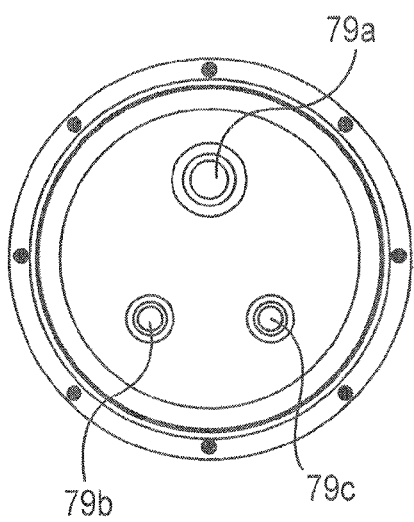
Figure 27B:
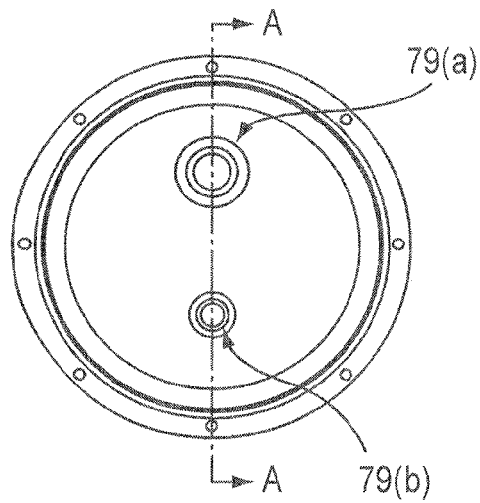
Figure 28:
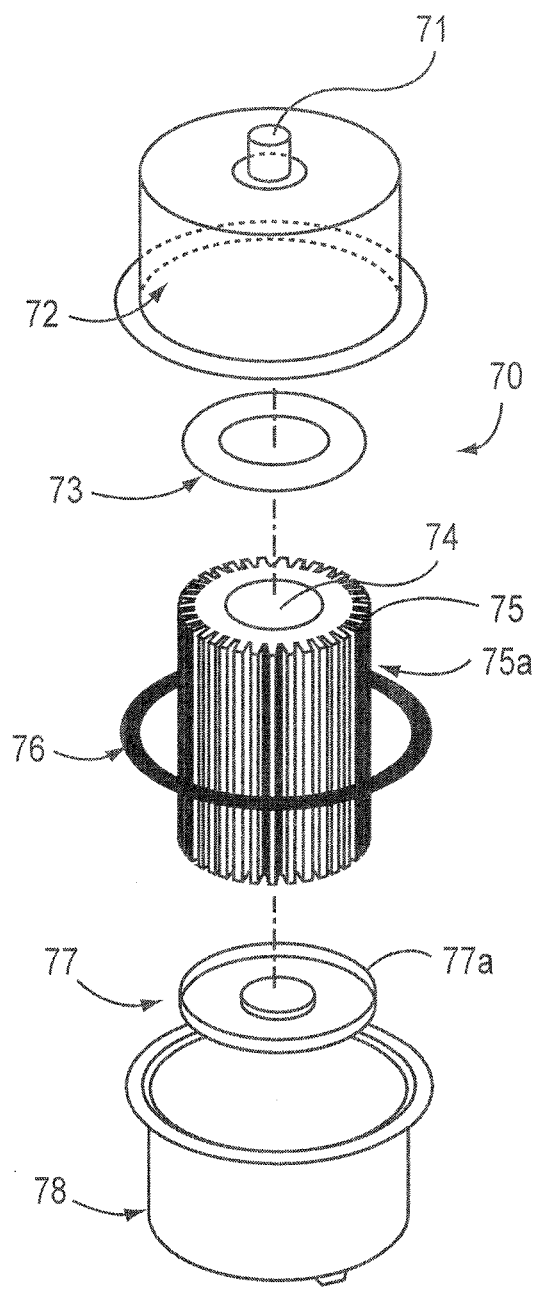

In certain variations, the system 10 may include a filter unit 70 (e.g., a HEPA filter) to prevent relatively large particles from entering the vacuum pump. Referring to FIGS. 26-28, the filter unit 70 may include a filter housing comprised of an first housing portion 72 and a second housing portion 78 configured to mate with one another to define a substantially enclosed interior space for receiving a filter 75. Although FIGS. 26-28 show housing portion 72 on top and housing portion 78 on bottom, this may be reversed. For example, FIG. 26 depicts the filter 70 with housing portion 72 as a lower housing portion and housing portion 78 as an upper housing portion. In this description, housing portion 72 will be referred to as the first housing portion and housing portion 78 as the second housing portion. The first housing portion 72 may define an outlet opening 71 for connection to a vacuum, for example, and the second housing portion 78 may define one or more inlet openings 79a, 79b, 79c for connection to various components utilizing the suction force generated by the vacuum pump. In such applications, the number of inlet openings 79a, 79b, 79c may depend upon the number of components that require connection to the vacuum pump. For example, if the system 10 includes only one component that requires connection to the vacuum pump, the second housing portion 78 may include only one inlet opening 79a. If, however, the system includes multiple components that require connections to the vacuum pump, the second housing portion 78 may include as many inlet openings 79a, 79b, 79c as needed by the system 10. For example, as shown in FIG. 27B the second housing portion may include two inlet openings.

The first housing portion 72 and the second housing portion 78 may be joined together via one or more screws, or other attachment features, such as a suitable snap-fastening or thread-fastening mechanism or any other suitable fastening mechanism. In the illustration shown in FIG. 28, a sealing gasket 76 may be disposed between the first housing portion 72 and the second housing portion 78 to seal the interface therebetween. The first housing portion 72 and the second housing portion 78 may be readily separable to facilitate replacement of the filter 75 disposed therein.

The filter 75 may comprise a microporous (HEPA-grade) material. The filter 75 may have a generally cylindrical shape defining a hollow internal space 74 in fluid communication with the outlet opening 71 of the first housing portion 72. The filter 75 may be formed of a hydrophobic material, such as expanded PTFE on thermally fused polyester (e.g., Tetratex® ePTFE available from Donaldson Company, Inc. of Minneapolis, Minn.). The filter 75 may have hydrophobic characteristics that serve as a safety valve for preventing water from flowing into the vacuum pump, for example.

In addition, only a portion of the filter may include a hydrophobic material. For example, one side of the filter may include hydrophobic material. The structure of the filter including only a portion of a hydrophobic material, alone or in combination with the other features, may allow the filter to continue to function even when a significant amount of liquid has entered the filter.

As shown in FIG. 28, the filter 75 may be positioned between an upper gasket 73 and an end cap 77. The upper gasket 73 may be made of polychloroprene material (e.g., neoprene) or microcellular urethane foam (e.g., Poron®), for example. The upper gasket 73 seals or partially seals the contact space between the top surface of the filter 75 and the first housing portion 72. In some exemplary variations, to enhance the sealing effect, the filter unit 70 may be configured such that, when the first housing portion 72 and the second housing portion 78 are joined together to compressibly enclose the filter unit 70, the filter 75 presses the upper gasket 73 so as to slightly compress the upper gasket 73.

The end cap 77 is configured to receive one end of the filter 75. The end cap 77 may define an annular groove 77a configured to receive the second end of the filter 75, for example, as shown in FIG. 28, for more securely holding the filter 75 in place. The end cap 77 is impermeable to fluid, thereby preventing any fluid from escaping via the first end of the filter 75. The space between the end cap 77 and the second housing portion 78 may define one or more flow paths (e.g., via reinforcement ribs extending radially). Thus, all of the fluid entering the filter unit 70 through the inlet openings 79a, 79b, 79c may flow around the end cap 77, pass through the side wall 75a of the filter 75, and exit the filter unit 70 through the internal space 74 and the outlet opening 71.

As noted above, smoke and/or gases may occur in connection with certain medical procedures. The filter is capable of filtering smoke and other undesirable gases from the air that is drawn into the liquid collection system and that passes through the filter.

Floor Suction Tool

Figure 30:
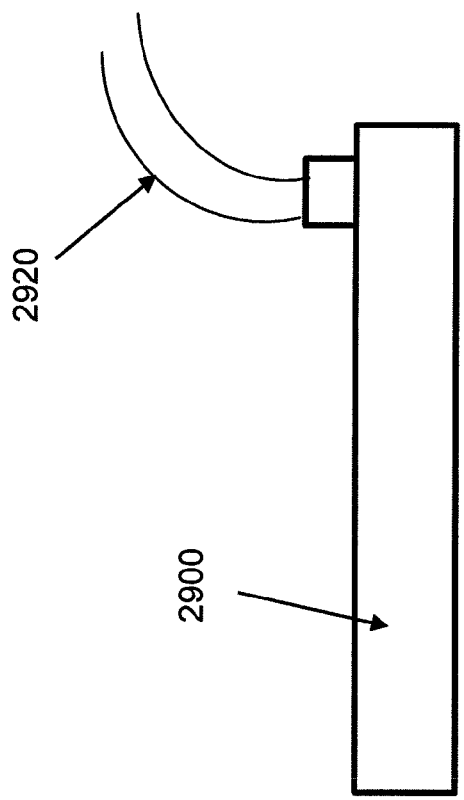
FIGS. 29-30 illustrate an exemplary flat surface suction tool, in accordance with aspects of the present invention.
Figure 29:
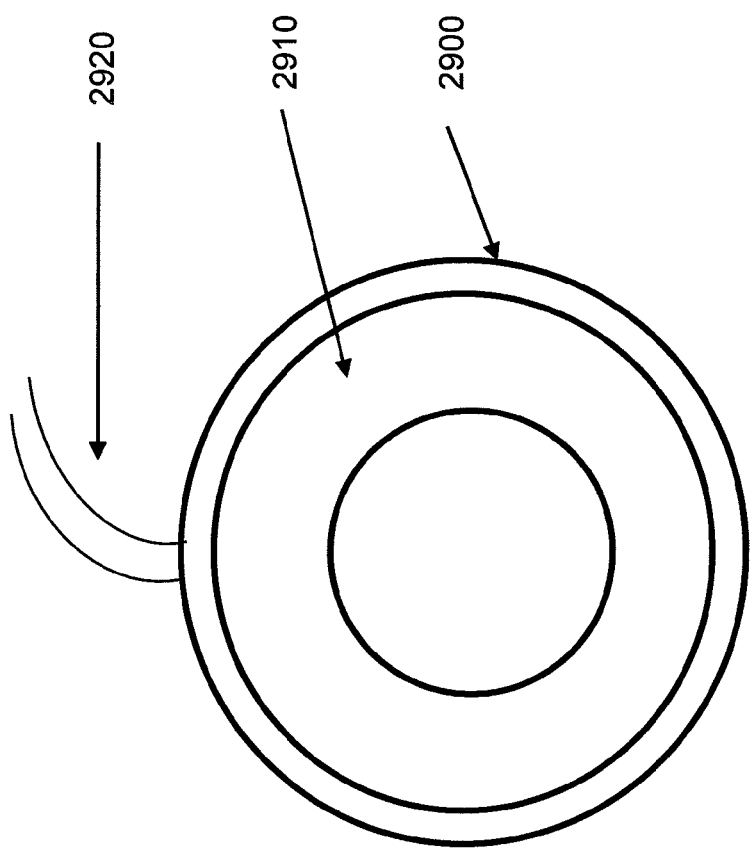

One example of a suction device to which the liquid collection container may be attached is a device for collecting fluid from a surface, such as a floor. During medical procedures, fluids may fall to the floor and require removal. FIGS. 29 and 30 illustrate an exemplary suction device for removing fluids from a surface. The suction device includes a housing 2900 and a porous material 2910 held in the housing. The housing 2900 includes an opening for receiving a connector 2920, such as tubing, that connects the device to a source of suction or vacuum. The tubing 2920 may be connected, for example, to one of the collection ports 32 on the liquid collection container. The housing 2900 is configured to communicate the suction or vacuum from the connector 2920 to the porous material 2921 so that fluid may be drawn through the porous material 221 and into the tubing 2920, and subsequently into a container. For example, the housing 2900 may include a channel that communicates vacuum pressure from the suction source and tubing 2920 to the porous material 2921. For example, the fluid may be drawn through the porous material 2921 into the tubing 2920 to a collection port 32 and into the disposable fluid collection container 30.

While aspects of the present invention have been described and illustrated with reference to one or more preferred variations thereof, it is not the intention of the applicants that these aspects be restricted to such detail. Rather, it is the intention of the applicants that aspects of the present invention be defined by all equivalents, both suggested hereby and known to those of ordinary skill in the art, of the variations falling within the scope thereof.

What is claimed is:

1. A fluid collection system, comprising:
    a disposable collection container having a flexible portion, a first opening for receiving fluid, and a second opening; and
    a receiving housing sized to receive the disposable collection container, the receiving housing including:
        a cavity into which the flexible portion of the disposable collection container expands;
        a suction source connectable to the second opening in the disposable collection container; and
        a piston assembly positioned within the cavity, wherein the piston assembly includes a main piston body and a scraper ring.

2. The fluid collection system according to claim 1, wherein the scraper ring includes a peripheral edge that extends above the main piston body and is configured to provide an interference fit with an interior surface of the cavity.

3. The fluid collection system according to claim 2, wherein the peripheral edge of the scraper ring is configured to flex against the interior surface of the cavity.

4. The fluid collection system according to claim 2, wherein the peripheral edge of the scraper ring extends from the main piston body to a height that enables the peripheral edge to conform to the interior surface of the cavity.

5. The fluid collection system according to claim 2, wherein the scraper ring is attached to the main piston body such that the peripheral edge of the scraper ring maintains contact with the interior surface of the cavity when the main piston body is off center.

6. The fluid collection system according to claim 2, wherein the piston assembly includes a support structure that supports the scraper ring.

7. The fluid collection system according to claim 6, wherein the support structure includes ribs formed in the scraper ring.

8. The fluid collection system according to claim 6, wherein the support structure includes ribs formed in the main piston body.

9. A fluid collection system, comprising:
a disposable collection container having a flexible portion; and
a receiving housing sized to receive the disposable collection container, the receiving housing including:
a cavity into which the flexible portion of the disposable collection container expands;
a suction source connectable to the disposable collection container; and
a piston assembly positioned within the cavity, wherein the piston assembly includes a main piston body, a scraper ring, and a valve assembly communicating between an area adjacent a first side of the piston and an area adjacent a second side of the piston, wherein the scraper ring includes a surface defining openings providing communication between an area between the first side of the piston and a first surface of the scraper ring and an area adjacent a second side of the scraper ring.

10. A fluid collection system, comprising:
a disposable collection container having a flexible portion; and
a receiving housing sized to receive the disposable collection container, the receiving housing including:
a cavity into which the flexible portion of the disposable collection container expands;
a suction source connectable to the disposable collection container; and
a piston assembly positioned within the cavity, wherein the piston assembly includes a main piston body and a scraper ring, wherein the scraper ring comprises an Ultra High Molecular Weight (UHMW) material.

11. The fluid collection system according to claim 10, wherein the UHMW material has a molecular weight of at least one million Daltons.

12. The fluid collection system according to claim 10, wherein the UHMW material comprises UHMW polyethylene.

13. The fluid collection system according to claim 1, wherein the scraper ring comprises a hydrophobic material.

14. The fluid collection system according to claim 1, wherein the cavity comprises a piston stop including:
a first opening in a cavity wall;
a second opening in the cavity wall; and
a channel connecting the first opening to the second opening, wherein the first opening is positioned above a desired piston stop height and the second opening is positioned below the desired piston stop height.

15. The fluid collection system according to claim 14, wherein the piston stop further includes a valve connected to the channel, wherein the valve has an open position to communicate a pressure differential through the channel between the first opening and the second opening and a closed position to prevent communication of a pressure differential between the first opening and the second opening.

16. A fluid collection system, comprising:
a disposable collection container having a flexible portion; and
a receiving housing sized to receive the disposable collection container, the receiving housing including:
a cavity into which the flexible portion of the disposable collection container expands;
a suction source connectable to the disposable collection container; and
a piston assembly positioned within the cavity, wherein the piston assembly includes a main piston body and a scraper ring,
wherein the cavity comprises a piston stop including:
a first opening in a cavity wall;
a second opening in the cavity wall;
a channel connecting the first opening to the second opening, wherein the first opening is positioned above a desired piston stop height and the second opening is positioned below the desired piston stop height;
a valve connected to the channel, wherein the valve has an open position to communicate a pressure differential through the channel between the first opening and the second opening and a closed position to prevent communication of a pressure differential between the first opening and the second opening; and
a third opening in the cavity wall,
wherein the channel connects the second opening to the third opening, and wherein the location between the second opening and the third opening is different one of a plurality of desired piston stop positions.

17. The fluid collection system according to claim 2, wherein the peripheral edge of the scraper ring is configured to prevent the flexible liner of the collection container from being pinched between an inner wall of the cavity and the main body of the piston.

* * * * *